United States Patent [19]
Gee et al.

[11] Patent Number: 5,830,912
[45] Date of Patent: Nov. 3, 1998

[54] DERIVATIVES OF 6,8-DIFLUORO-7-HYDROXYCOUMARIN

[75] Inventors: Kyle R. Gee, Springfield; Richard P. Haugland; Wei-Chuan Sun, both of Eugene, all of Oreg.

[73] Assignee: Molecular Probes, Inc., Eugene, Oreg.

[21] Appl. No.: 749,684

[22] Filed: Nov. 15, 1996

[51] Int. Cl.$^6$ .................. A61K 31/37; C07D 311/14; C07D 311/16
[52] U.S. Cl. ............. 514/457; 549/283; 549/285; 549/287; 549/289
[58] Field of Search .................... 549/289, 283, 549/285, 287; 514/457

[56] References Cited

U.S. PATENT DOCUMENTS

| | | | |
|---|---|---|---|
| 2,844,594 | 7/1958 | Long et al. | 260/343.2 |
| 3,014,041 | 12/1961 | Hieusermann et al. | 260/394 |
| 4,997,928 | 3/1991 | Hobbs, Jr. et al. | 536/27 |
| 5,049,673 | 9/1991 | Tsien et al. | 546/107 |
| 5,171,534 | 12/1992 | Smith et al. | 422/82.05 |
| 5,196,306 | 3/1993 | Bobrow et al. | 435/7.9 |
| 5,332,666 | 7/1994 | Prober et al. | 435/91.5 |
| 5,362,628 | 11/1994 | Haugland et al. | 435/18 |
| 5,405,975 | 4/1995 | Kuhn et al. | 549/347 |
| 5,453,517 | 9/1995 | Kuhn et al. | 549/227 |
| 5,459,268 | 10/1995 | Haugland et al. | 546/37 |
| 5,516,911 | 5/1996 | London et al. | 548/236 |
| 5,576,424 | 11/1996 | Mao et al. | 536/17.9 |

FOREIGN PATENT DOCUMENTS

| | | |
|---|---|---|
| 0 185 319 B1 | 6/1989 | European Pat. Off. . |
| WO 94/05688 | 3/1994 | WIPO . |

OTHER PUBLICATIONS

Chemical Abstract, 122 : 105,666n, 1995.
Fomenko, et al., Izv. Sib. Otd. Akad. Nauk SSSR, Ser. Khim. Nauk 2, 127 (1981).
Wittung, et al., Nature 368, 561 (1994).
Raju, et al., Am. J. Physiol. 256, C540 (1989).
Hermanson, Bioconjugates Techniques, Academic Press (1996).
Haugland, Molecular Probes Handbook of Fluorescent Probes and Research Chemicals, Sets 1–7 (1992).
Brinkley, M., Bioconjugate Chem. 3, p. 2 (1992).
Haugland, R. Meth. Mol. Biol. 45, p. 205 (1995).
H. von Pechmann, et al., Chem. Ber. 16, p. 2119 (1883).
Sethna, et al., Org. React. 7, p. 1 (1953).
Hamprecht, et al., Ca Selects: Colorants and Dyes 23, p. 125: 221838f (1996).
Wolfbeis, et al., Chem. Ber., 118, p. 3664 (1985).
Machida, et al., Chem. Pharm. Bull. 23, p. 1385 (1975).
Sippel, T.J. Histochem. Cytochem. 29, p. 314 (1981).

*Primary Examiner*—Ba K. Trinh
*Attorney, Agent, or Firm*—Allegra J. Helfenstein; Anton E. Skaugset

[57] ABSTRACT

The present invention comprises 6,8-difluoro-7-hydroxycoumarins and derivatives of 6,8-difluoro-7-hydroxycoumarins, including reactive dyes, dye-conjugates and enzyme substrates. These fluorine-substituted fluorescent dyes typically possess greater photostability and lower pH sensitivity in the physiological pH range than their nonfluorinated analogs, exhibit less fluorescence quenching when conjugated to a substance, possess absorption and emission spectra that closely match those of their nonfluorinated analogs, and also exhibit higher quantum yields than their nonfluorinated analogs.

35 Claims, 11 Drawing Sheets

DERIVATIVES OF 6,8-DIFLUORO-7-HYDROXYCOUMARIN

FIELD OF THE INVENTION

The invention relates to derivatives of 6,8-difluorinated coumarin fluorophores, including chemically reaction fluorophores, conjugates of fluorophores, and fluorogenic enzyme substrates; as well as uses of the fluorinated coumarin compounds and their derivatives.

BACKGROUND OF THE INVENTION

Fluorescent dyes are known to be particularly suitable for biological applications in which a highly sensitive detection reagent is desirable. Fluorescent dyes are used to impart both visible color and fluorescence to other materials.

Hydroxy-substituted coumarins have been widely used in the preparation of fluorescent dye-conjugates and fluorescent-labeled enzyme substrates. 7-Hydroxy-4-methylcoumarin (also known as 4-methylumbelliferone) is the parent compound for the preparation of a number of fluorogenic enzyme substrates. Phosphorylation of the 7-hydroxy group gives a phosphate monoester (MUP) that has been extensively used to detect the enzymes alkaline phosphatase and acid phosphatase. Additionally, 4-methylumbelliferyl p-guanidinobenzoate has been used to determine concentrations of the serine proteases trypsin, thrombin and factor Xa. Numerous fluorogenic glycosidase substrates have been prepared based on 4-methylumbelliferone, including the 4-methylumbelliferyl galactopyranoside (MUG), glucopyranoside and glucuronide.

However, 7-hydroxycoumarins and their conjugates are typically not fully deprotonated (and therefore not maximally fluorescent) unless the dye is present in an environment having a pH of 9 or higher. The sensitivity of assays using 7-hydroxycoumarin-based enzyme substrates therefore suffers at lower pH, e.g. where some or all of the assay components are incompatible with basic pH levels. The sensitivity of assays for glycosidases and acid phosphatases is therefore limited, as these enzymes have optimal turnover rates at or below neutral pH. Similarly, many protein conjugates of 7-hydroxycoumarin are unstable with respect to the basic conditions required to obtain maximal fluorescence of the label. In addition, dye-conjugates of 7-hydroxycoumarins typically exhibit self-quenching at high degrees of substitution.

The compounds of the present invention are derivatives of 6,8-difluoro-7-hydroxycoumarin that possess a variety of advantages relative to their nonfluorinated and even monofluorinated analogs (see Table 3). The compounds of the present invention possess enhanced photostability relative to their nonfluorinated analogs, with little or no shift in either absorbance or emission wavelengths. In addition, the 6,8-difluorinated 7-hydroxycoumarins possess substantially lower sensitivity to pH effects in the physiological pH range (i.e. pH 6–8) than their nonfluorinated coumarin analogs. This property is particularly useful for investigating enzyme systems that require low pH conditions, for example acid phosphatase and β-galactosidase. In addition, the 6,8-difluorinated coumarin dye-conjugates of the invention, in particular the protein conjugates, exhibit very bright fluorescence even at relatively high degrees of dye substitution. Additionally, the enzyme substrates of the invention give brighter reaction products, and in many cases provide greater rates of enzyme turnover than their nonfluorinated analogs.

While a variety of fluorinated coumarins have been described in the literature, the particularly advantageous fluorophore 6,8-difluoro-7-hydroxy-4-methylcoumarin has not been described. Dye-conjugates of fluorinated 7-hydroxycoumarins have also not previously been described; in particular no dye-conjugates of 6,8-difluoro-7-hydroxycoumarins have previously been described.

The preparations of compounds 7-methoxy-5,6,8-trifluorocoumarin and 7-hydroxy-5,6,8-trifluorocoumarin were described by Fomenko et al. (IZV. SIB. OTD. AKAD. NAUK SSSR, SER. KHIM. NAUK 2, 127 (1981)). However, these trifluorinated hydroxycoumarin derivatives possess a much lower quantum yield than the difluorinated hydroxycoumarins of the present invention, lower even than their nonfluorinated analogs (see Table 3).

In addition, Gondolfi et al. (European Patent Specification 0 185 319 B1) describes a variety of fluorinated coumarins as antilymphoedema agents, but none of the compounds of Gondolfi et al. are 7-hydroxycoumarins. It is well known that the 7-hydroxy substituent is required to produce the useful long wavelength fluorescence of the dyes, as well as providing a means for preparing the useful enzyme substrates of the present invention. In addition, there is no description in the reference of the use of fluorinated coumarins to prepare dye-conjugates.

Figure 9:
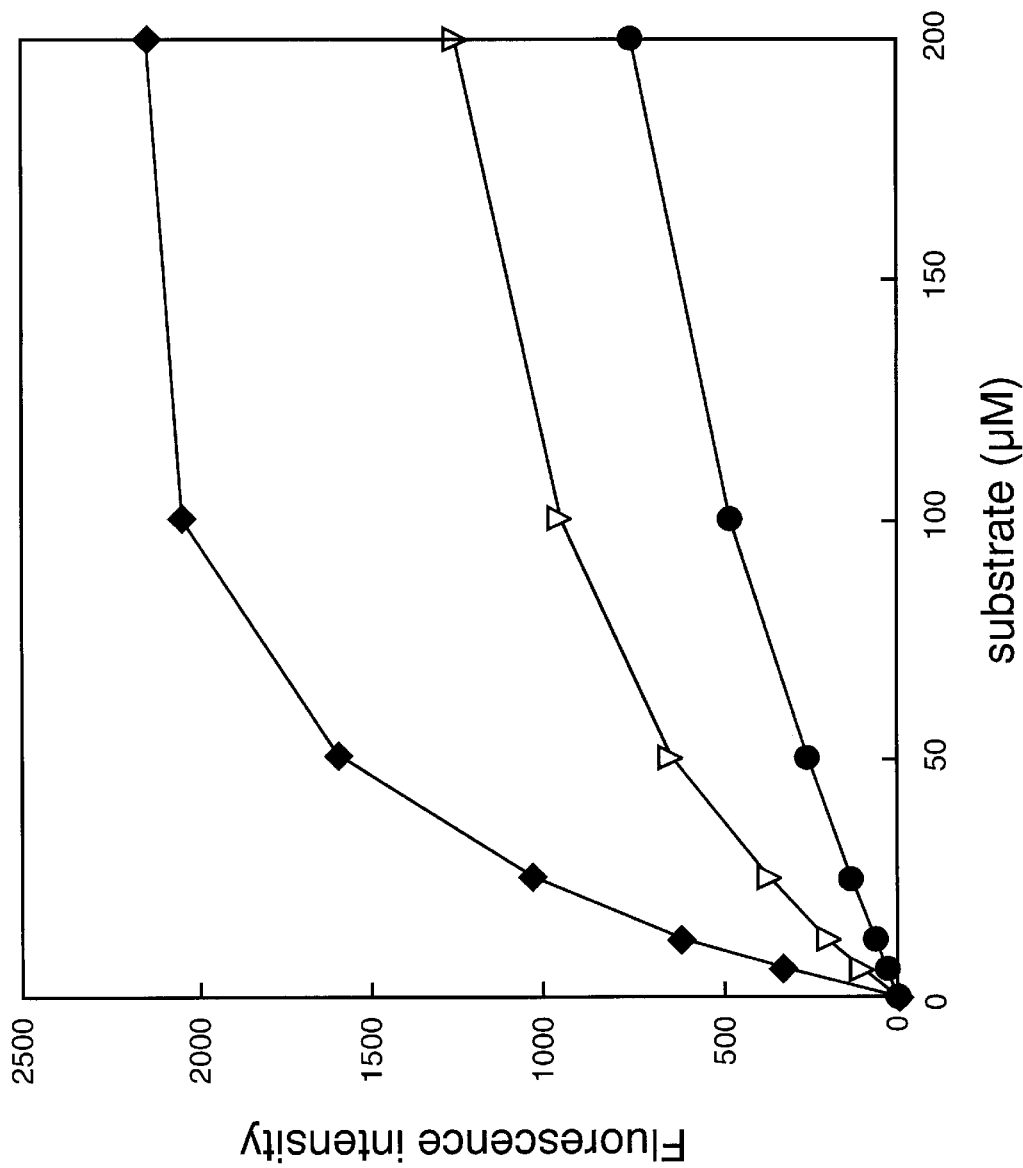

FIG. 9: The determination of the Michaelis-Menton constant ($K_m$) for galactosidase substrates Compound 9 at pH 7 (♦), MUG at pH 7(●), and MUG at pH 10 (▽). As described in Example 47, $K_m$ for Compound 9 is about 25 μM, whereas that derived for MUG is about 60 μM.

Figure 10:
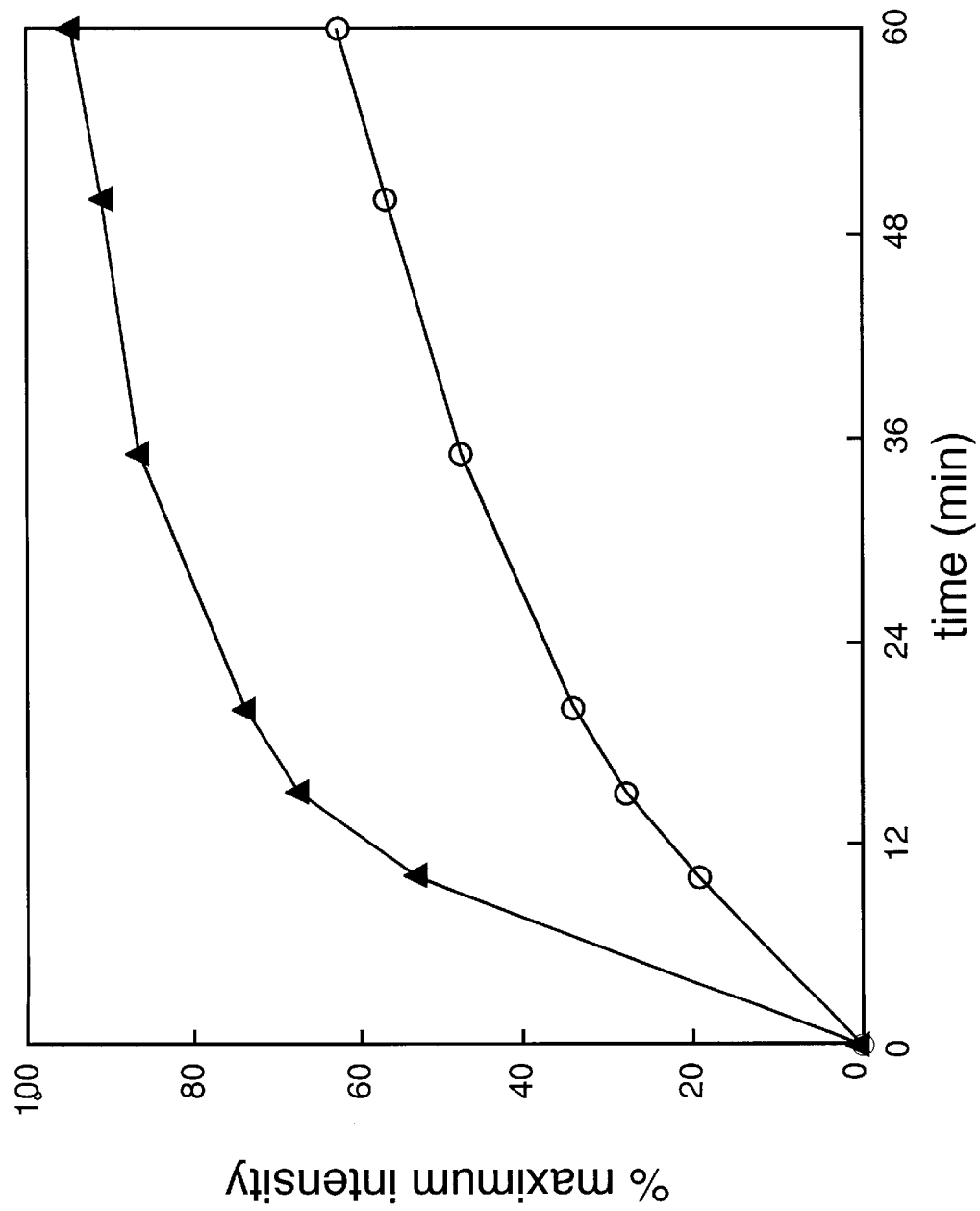

FIG. 10: A comparison of initial reaction rate of β-galactosidase with respect to galactosidase substrates Compound 9 (▲) and MUG (○), as described in Example 47.

Figure 11:
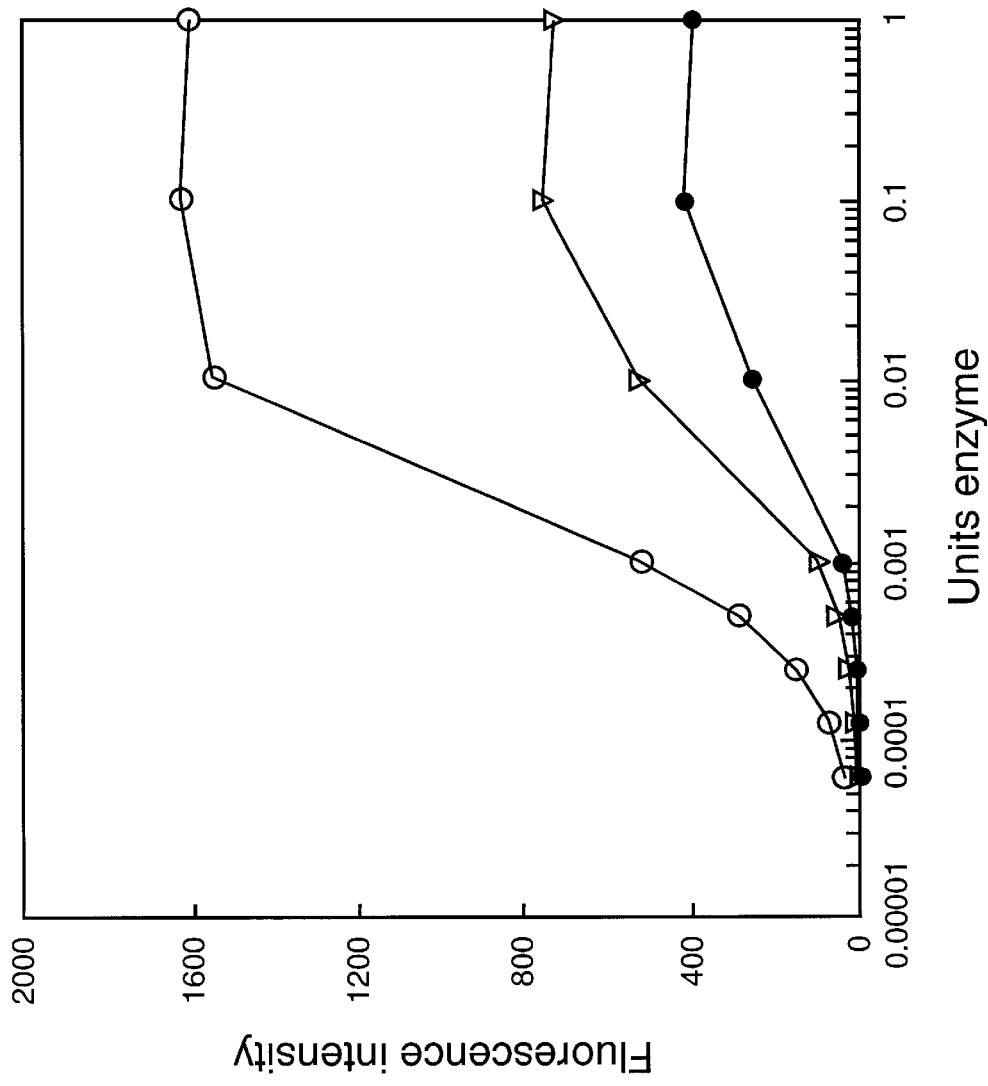

FIG. 11: A comparison of sensitivity of β-galactosidase detection possible using galactosidase substrates Compound 9 at pH 7 (○), MUG at pH 7 (●), and MUG at a final pH of 10 (▽). As described in Example 47, the use of Compound 9 allows the detection of significantly lower amounts of β-galactosidase enzyme.

SUMMARY OF THE INVENTION AND DESCRIPTION OF THE PREFERRED EMBODIMENTS

The present invention comprises 6,8-difluoro-7-hydroxycoumarins and derivatives of 6,8-difluoro-7-hydroxycoumarins, including reactive dyes, dye-conjugates and enzyme substrates. These fluorine-substituted fluorescent dyes typically possess greater photostability and lower pH sensitivity in the physiological pH range than their nonfluorinated analogs, exhibit less fluorescence quenching when conjugated to a substance, possess absorption and emission spectra that closely match those of their nonfluorinated analogs, and also exhibit higher quantum yields than their nonfluorinated analogs.

As used herein, alkyl refers to a hydrocarbon that is optionally linear or branched and saturated or unsaturated. Similarly, the alkyl portions of perfluoroalkyl, alkoxy, alkylthio, monoalkylamino, dialkylamino or alkylamido groups are optionally linear or branched, saturated or unsaturated.

As used herein, an aryl is a phenyl moiety that is optionally and independently substituted by H, halogen, cyano, azido, sulfonic acid, alkali or ammonium salt of sulfonic acid, carboxylic acid, biologically compatible salt of carboxylic acid, nitro, alkyl, perfluoroalkyl, alkoxy, alkylthio, amino, monoalkylamino, dialkylamino or alkylamido. Preferred aryl groups are phenyl and perfluorophenyl.

As used herein, a heteroaryl is a 5- or 6-membered aromatic heterocycle that is optionally fused to an additional six-membered aromatic ring or to one 5- or 6-membered heteroaromatic ring, said heteroaromatic ring containing 1–3 heteroatoms that are selected from the group consisting of O, N and S in any combination. Any heteroaryl substituent is attached by a single bond, and is optionally and independently substituted one or more times by H, halogen, alkyl having 1–6 carbons, or alkoxy having 1–6 carbons. Selected examples of heteroaryl substituents are pyrrole, thiophene, or furan (single ring, single hetero atom), oxazole, isoxazole, oxadiazole, or imidazole (single ring, multiple hetero atoms). Examples of multi-ring heteroaryl groups include benzoxazole, benzothiazole, benzimidazole (multi-ring, multiple hetero atoms), benzofuran or indole (multi-ring, single hetero atom). Preferred heterocycles are 2-benzothiazolyl or 2-benzoxazolyl.

As used herein, a biologically compatible salt is a counterion that is not toxic as used, and does not have a substantially deleterious effect on biomolecules. Examples of biologically compatible salts include, among others, $K^+$, $Na^+$, $Cs^+$, $Li^+$, $Ca^{2+}$, $Mg^{2+}$, and alkylammonium or alkoxyammonium salts.

The compounds of the present invention have the general formula

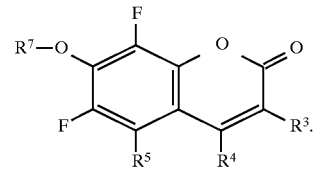

The substituent $R^3$ is H, an alkyl having 1–18 carbons, a perfluoroalkyl having 1–18 carbons, a cyano, an aryl, a heteroaryl, an arylcarbonyl, formyl, or a carboxamide of the formula —(C═O)—$NR^1R^2$ where $R^1$ and $R^2$ are independently H, alkyl having 1–6 carbons, an aryl, or $R^1$ and $R^2$ when taken in combination form a saturated 5- or 6-membered ring having the formula —(CH$_2$)$_2$—M—(CH$_2$)$_2$— where the ring moiety M is a single bond, an oxygen atom, a methylene group, or the secondary amine —$NR^6$—, where $R^6$ is H or alkyl having 1–6 carbons. Alternatively, the $R^3$ substituent is a covalently attached reactive group having the formula —L—$R_x$, or a covalently attached conjugated substance having the formula —L—$S_C$.

The substituent $R^4$ is H, cyano, an alkyl having 1–18 carbons, a perfluoroalkyl having 1–18 carbons, sulfomethyl or a biologically compatible salt of sulfomethyl, or an aryl. Alternatively, the $R^4$ substituent is a covalently attached reactive group having the formula —L—$R_x$, or a covalently attached conjugated substance having the formula —L—$S_C$. In one embodiment of the invention, $R^4$ is sulfomethyl, salt of sulfomethyl, halomethyl, alkyl having 1–18 carbons or perfluoroalkyl having 1–18 carbons.

The substituent $R^5$ is H or an alkoxy group having 1–6 carbons. Typically, $R^5$ is H.

The substituent $R^7$ is H, in which case the resulting hydroxycoumarin dye possesses long-wavelength fluorescence properties, or $R^7$ is a monovalent moiety that interferes with or alters the long-wavelength fluorescence properties of the coumarin until the moiety is removed. In this embodiment, $R^7$ is typically a monovalent moiety selected to cleavable by action of an enzyme, and the resulting dyes are useful analytical tools for detecting and/or quantifying selected enzymes. In one embodiment, $R^7$ is a monovalent moiety that is formally derived by removal of a hydroxy group from a phosphate, a thiophosphate, a sulfate, or a biologically compatible salt thereof. Typically, the dyes of the invention wherein $R^7$ is derived from phosphate or thiophosphate are useful as phosphatase substrates. Preferably, $R^7$ is a monovalent moiety derived by the removal of a hydroxy group from a guanidinobenzoic, phosphoric, or sulfuric acid, or a biologically compatible salt thereof.

In another embodiment, $R^7$ is a monovalent moiety that is formally derived by removal of a hydroxy group from a carboxy group of an aliphatic or aromatic carboxylic acid. In yet another embodiment, $R^7$ is a monovalent moiety that is formally derived by removal of a hydroxy group from an alcohol (preferably having 6 or fewer carbons, or a steroidal alcohol) or from a mono- or polysaccharide. Dyes of the invention wherein $R^7$ is derived from a mono- or polysaccharide are typically useful as glycosidase substrates, while dyes of the invention wherein $R^7$ is derived from a lower alcohol are typically useful as dealkylase substrates. Where $R^7$ is derived from a monosaccharide, preferably the monosaccharide is β-D-galactose, β-D-glucose, β-D-glucuronic acid, N-acetylglucosamine, or N-acetylgalactosamine.

In another embodiment of the invention, $R^7$ is a photo-labile caging group that is cleavable by exposure to light of an appropriate wavelength. The caging group is selected so as to partially or maximally interfere with the fluorescence properties of the dye until photolysis restores the free hydroxycoumarin dye. Preferably, the caging group essentially quenches the dyes' fluorescence properties. In one embodiment of the invention, the photolabile caging group is a derivative of o-nitroarylmethine having the formula:

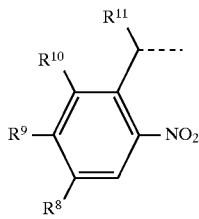

where $R^8$ and $R^9$ are independently H, alkoxy having 1–6 carbons, —O(CH$_2$)$_v$CO$_2$R$^{13}$ (where v=1–18 and $R^{13}$ is H or alkyl having 1–6 carbons) or $R^8$ taken in combination with $R^9$ is methylenedioxy (—O—CH$_2$—O—). $R^{10}$ is H or NO$_2$. $R^{11}$ is H, CH$_3$, or CO$_2$R$^{12}$, where $R^{12}$ is H, a biologically compatible esterifying group, or a biologically compatible salt. Caging moieties that are alpha-carboxy nitroarylmethines (compounds wherein $R^{11}$ is CO$_2$R$^{12}$) have been previously described in Copending Application ALPHA-CARBOXY CAGED COMPOUNDS, Ser. No. 08/336,284, filed Nov. 8, 1994 (incorporated by reference). In one embodiment of the invention, $R^{11}$ is CH$_3$ and $R^{10}$ is H. In another embodiment of the invention, $R^8$ and $R^9$ are each methoxy.

In another embodiment of the invention, the photolabile caging group is a derivative of desyl having the formula:

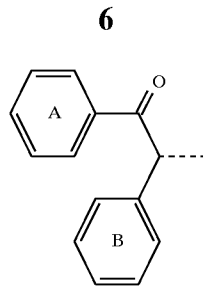

where aromatic rings A and B are optionally and independently substituted one or more times by halogen, —NO$_2$, —OR$^{14}$, and —NR$^{15}$R$^{16}$ where $R^{14}$, $R^{15}$ and $R^{16}$ are independently alkyl groups having 1–6 carbons. Preferably there are no more than two non-hydrogen substituents on each of rings A and B.

The moiety L is a covalent linkage, the moiety $R_X$ is a reactive group, and the moiety $S_C$ is a conjugated substance. Those compounds for which at least one of $R^3$ and $R^4$ is —L—R$_X$ are reactive dyes, while those compounds for which at least one of $R^3$ and $R^4$ is —L—S$_C$ are dye-conjugates. Each of these dye components is described in greater detail below.

In one embodiment of the invention, $R^3$ or $R^4$ is —L—R$_X$, preferably $R^3$ is —L—R$_X$. In another embodiment of the invention, $R^3$ or $R^4$ is —L—S$_C$, preferably $R^3$ is —L—S$_C$. In an additional embodiment of the invention, $R^3$ or $R^4$ is —L—R$_X$ or —L—S$_C$ and $R^7$ is a monovalent moiety selected to be cleavable by action of an enzyme. Typically if $R^3$ is —L—R$_X$, then $R^4$ is methyl and, if $R^4$ is —L—R$_X$, then $R^3$ is H.

In a preferred embodiment, $R^3$ is H, $R^4$ is methyl, trifluoromethyl, or chloromethyl, $R^5$ is H and $R^7$ is H or a monovalent moiety derived by removal of a hydroxy group from a phosphate or a biologically compatible salt of phosphate; or a monovalent moiety derived by removal of a hydroxy group from a monosaccharide that is β-D-galactose, β-D-glucose, β-D-glucuronic acid, N-acetylglucosamine, or N-acetylgalactosamine.

Selected embodiments of the present invention are given in Table 1.

TABLE 1

Selected embodiments of the dyes of the invention

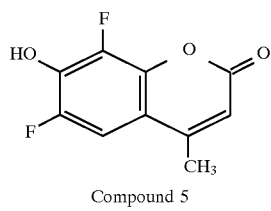

Compound 5

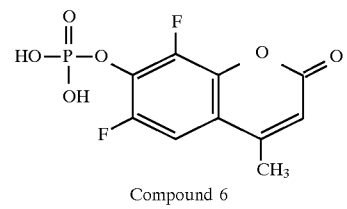

Compound 6

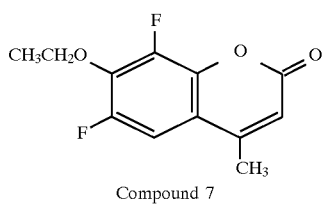

Compound 7

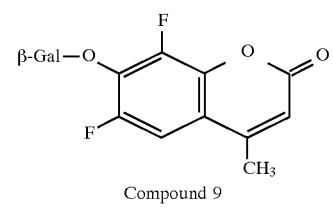

Compound 9

TABLE 1-continued
Selected embodiments of the dyes of the invention
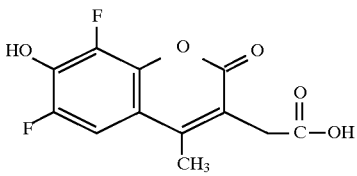
Compound 11
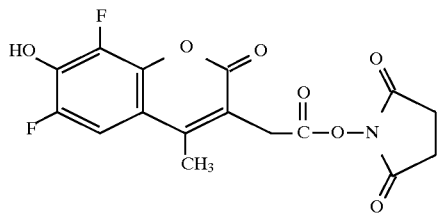
Compound 12
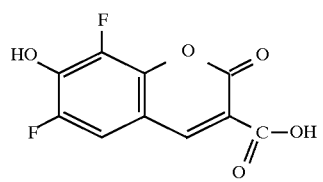
Compound 15
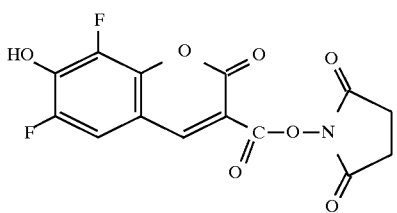
Compound 16
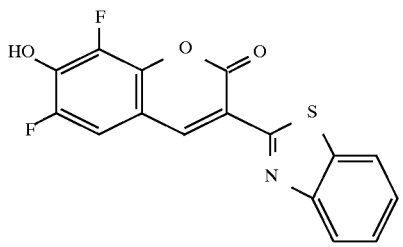
Compound 17
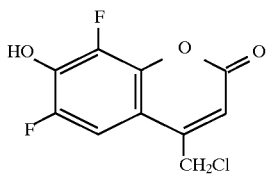
Compound 28
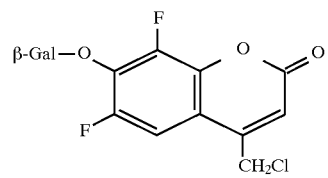
Compound 29
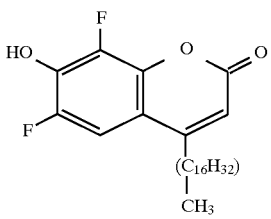
Compound 30
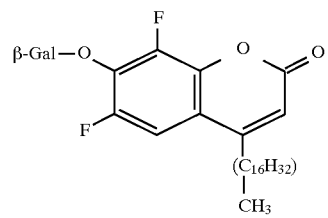
Compound 31
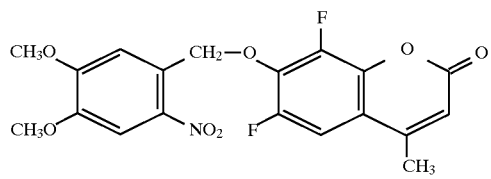
Compound 36
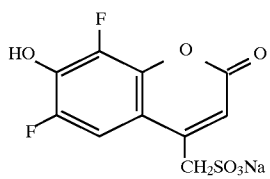
Compound 37
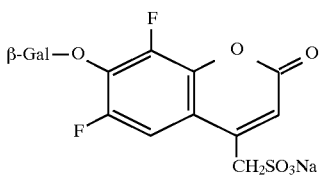
Compound 39

TABLE 1-continued
Selected embodiments of the dyes of the invention
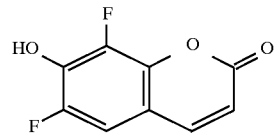
Compound 50
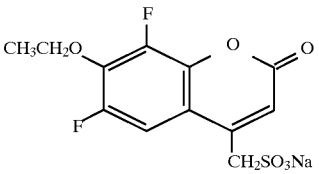
Compound 51
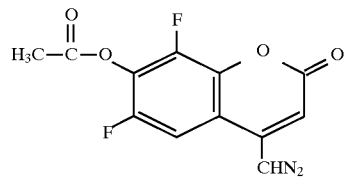
Compound 52
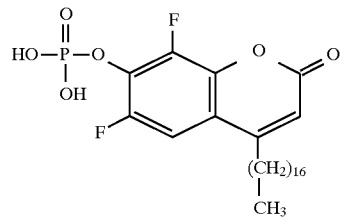
Compound 53
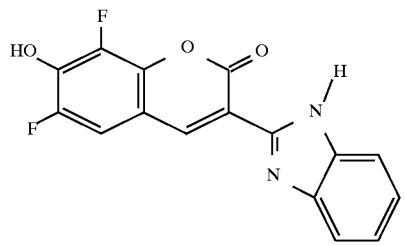
Compound 54
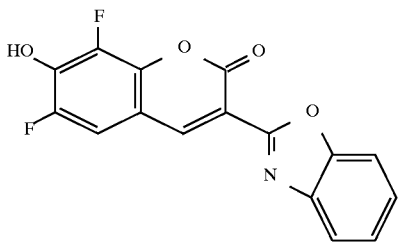
Compound 55
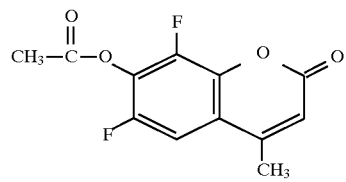
Compound 56
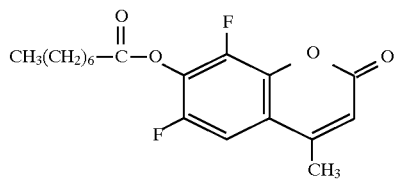
Compound 57
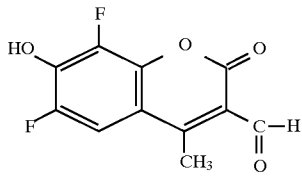
Compound 58
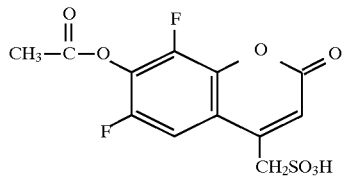
Compound 59
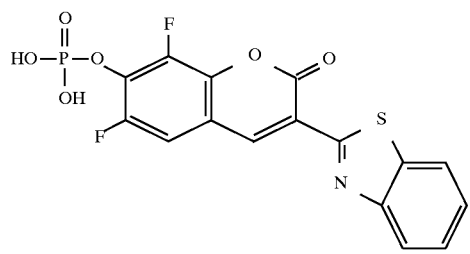
Compound 60
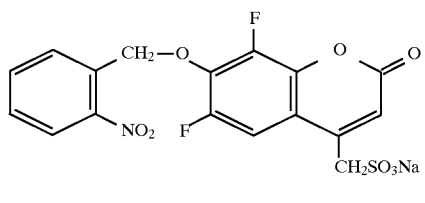
Compound 61

TABLE 1-continued

Selected embodiments of the dyes of the invention

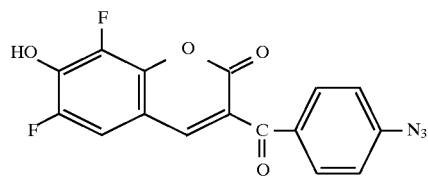

Compound 62

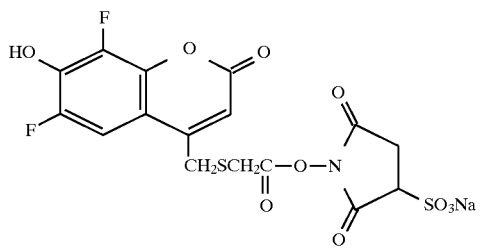

Compound 63

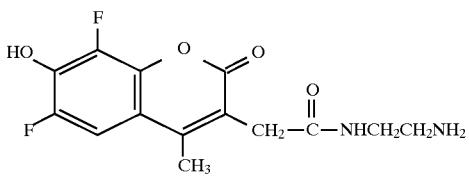

Compound 64

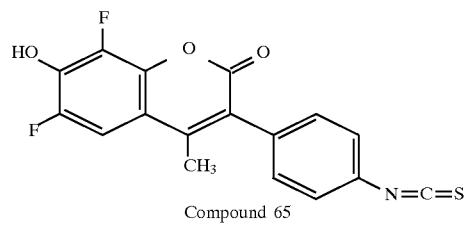

Compound 65

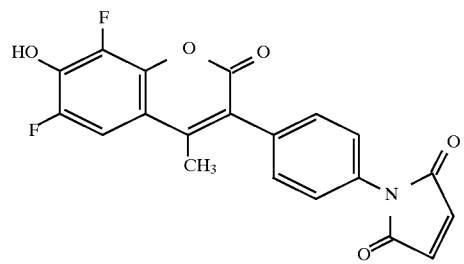

Compound 66

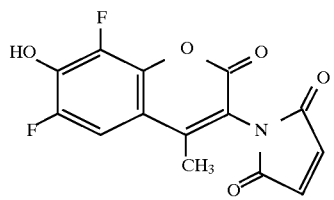

Compound 67

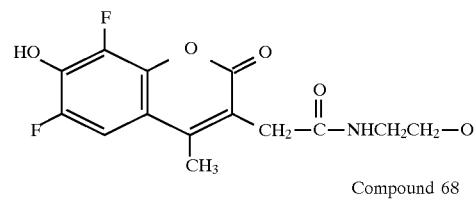

Compound 68

Conjugates of Reactive Dyes

The dyes of the invention with a reactive group ($R_x$) fluorescently label a wide variety of organic or inorganic substances that contain or are modified to contain functional groups with suitable reactivity, resulting in chemical attachment of the conjugated substance ($S_c$). The reactive group and functional group are typically an electrophile and a nucleophile that can generate a covalent linkage. Alternatively, the reactive group is a photoactivatable group, and becomes chemically reactive only after illumination with light of an appropriate wavelength. Selected examples of functional groups and linkages are shown in Table 2, where the reaction of an electrophilic group and a nucleophilic group yields a covalent linkage.

Table 2: Examples of some routes to useful covalent linkages

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |

-continued

| Electrophilic Group | Nucleophilic Group | Resulting Covalent Linkage |
|---|---|---|
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl ($-OC_4H_4O_2$) oxysulfosuccinimidyl ($-OC_4H_3O_2-SO_3H$), -1-oxybenzotriazolyl ($-OC_6H_4N_3$); or an aryloxy group or aryloxy substituted one or more times by electron withdrawing substituents such as nitro, fluoro, chloro, cyano, or trifluoromethyl, or combinations thereof used to form activated aryl esters; or a carboxylic acid activated by a carbodiimide to form an anhydride or mixed anhydride $-OCOR^a$ or $-OCNR^aNHR^b$, where $R^a$ and $R^b$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).
**Acyl azides can also rearrange to isocyanates The covalent linkage L binds the reactive group $R_X$ or conjugated substance $S_C$ to the fluorophore, either directly or with a combination of stable chemical bonds, optionally including single, double, triple or aromatic carbon-carbon bonds, as well as carbon-nitrogen bonds, nitrogen—nitrogen bonds, carbon-oxygen bonds and carbon-sulfur bonds. Generally, L moieties have 1–24 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably, L is a single covalent bond or the longest linear segment of the linkage L preferably contains 4–10 nonhydrogen atoms, of which two or fewer are heteroatoms; and comprises one or more carbonyl, carboxamide, polymethylene, arylene or heteroarylene linkages; or an ether or thioether linkage. Carbonyl means —(C=O)—; carboxamide means —(C=O)—NH— or —NH—(C=O)—; polymethylene means —(CH$_2$)$_n$—, where n=1–12; preferably n=1–5; phenylene means —(C$_6$H$_4$)—, where the points of attachment are typically para to each other on the phenyl ring. An ether or thioether has the formula —(CH$_2$)$_a$—Y—(CH$_2$)$_b$, where a=0–5, b=1–5, and Y is O or S. In yet another embodiment of the invention, L has the formula —(CH$_2$)$_a$—((C=O)—NH—(CH$_2$)$_b$)$_z$—, where a and b are as defined above, and z is 0 or 1.

The selection of covalent linkage to attach the coumarin to the conjugated substance typically depends on the functional group on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. Although some selectivity can be obtained by careful control of the reaction conditions, selectivity of labeling is best obtained by selection of an appropriate reactive dye.

Typically, $R_X$ is an acrylamide, a carboxylic acid, an activated ester of a carboxylic acid, an acyl azide, an acyl halide, a hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, or a thiol group. Preferably, $R_X$ is a carboxylic acid, an activated ester of a carboxylic acid, a hydroxy, an aldehyde, an alkyl halide, an amine, a haloacetamide, a halotriazine, a hydrazine, an isothiocyanate, a maleimide, or a thiol group.

For conjugation to substances having free amine groups, typically dyes are selected wherein L is either a single chemical bond, or L is —(CH$_2$)$_a$—, or L is —(CH$_2$)$_a$—(C=O)(NH(CH$_2$)$_b$)$_z$— or L is —(CH$_2$)$_a$—Y—(CH$_2$)$_b$— (where a, b, z and Y are as defined previously) and $R_X$ is a carboxylic acid or is an activated ester of a carboxylic acid (which is preferably a succinimidyl ester, including sulfosuccinimidyl esters). Examples of amine-reactive dyes include Compounds 12, 16, and 63 in Table 1. Amine-reactive dyes are of particular relevance as they are commonly used to label proteins and polypeptides, which possess free amine groups, or for chemical derivatization of amines to be analyzed by chromatographic or electrophoretic means. Amine-reactive dyes are additionally used to label materials that have been substituted with free amine groups, such as amino-dextrans, or amine-containing nucleotides, oligonucleotides, nucleic acids, amine-derivatized polymers or glasses, amine-containing haptens, or amine-containing drugs.

For conjugation to free thiol groups, dyes of the invention typically have $R_X$ as a haloalkyl (particularly halomethyl), haloacetamide, halomethylbenzamide, a maleimido group, an epoxide or a sulfonate ester, wherein the sulfonic acid is an alkylsulfonic acid, perfluoroalkylsulfonic acid or an arylsulfonic acid. Preferred thiol-reactive dyes of the invention are those wherein $R^3$ is —L—$R_X$ and $R_X$ is maleimido or haloacetamido. Additional preferred thiol-reactive dyes of the invention are those wherein $R^4$ is —L—$R_X$ and $R_X$ is —CH$_2$Cl or —CH$_2$Br or $R_X$ is maleimido, bromoacetamido or iodoacetamido. Examples include Compounds 28, 29, 66, and 67 in Table 1.

Preferred aldehyde- and ketone-reactive groups are hydrazines and carbohydrazides.

Dye-conjugates prepared using photoreactive dyes of the invention (wherein $R_X$ is an azide, diazirinyl, azidoaryl (including azidoperfluoroaryl) derivative) require illumination with a suitable wavelength, typically <400 nm. Preferred photoreactive groups are azidotetrafluorophenyl or azidotetrafluorobenzoyl. Alternatively, dye-conjugates containing photoreactive groups (either of the azide, diazirinyl or azidoaryl photocrosslinking type or of those wherein $R^7$ is a caging moiety) are prepared from derivatives that have an additional reactive moiety —L—$R_X$.

Useful dye-conjugates of the present invention include conjugates of antigens, steroids, vitamins, metabolites, toxins, environmental pollutants, amino acids, tyramine, peptides, proteins, nucleic acids, nucleic acid polymers, carbohydrates, lipids, ion-complexing moieties, polymers, or cells or cellular components. Typically, the dye-conjugates are conjugates of peptides or proteins; nucleotides, or nucleic acid polymers; lipids; mono- or polysaccharides; therapeutic drugs and drugs of abuse; and pesticides.

Alternatively, the conjugates of the present invention are conjugates of cells, cellular systems, cellular fragments, or subcellular particles. Typically, in this embodiment of the invention the conjugated materials include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

Most preferably, the conjugated substance is an amino acid, peptide, protein, polysaccharide, ion-complexing moiety, nucleotide, oligonucleotide, nucleic acid, hapten, drug, lipid, phospholipid, lipoprotein, lipopolysaccharide, liposome, lipophilic polymer, polymeric microparticle, animal cell, plant cell, bacterium, yeast or virus.

In one embodiment of the invention, the conjugated substance ($S_C$) is an amino acid or a polymer of amino acids such as a peptide or protein. Amino acids mean natural amino acids or their optical isomers, as well as synthetic variations utilized in the art. Common synthetic variations include amino acids that are protected on their amino, carboxylic acid, hydroxy, thiol, imidazole or other functional group. Other modified amino acids are substituted by phosphate, or through glycosylation or acylation with a $C_1$ to $C_{22}$ carboxylic acid. Peptides generally have molecular weights of less than about 5,000 to 10,000 daltons, and proteins have molecular weights greater than about 5,000 to 10,000 daltons and typically possess secondary, tertiary and/or quaternary structure. Preferred conjugates of peptides contain at least five amino acids, more preferably 5 to 36 amino acids. Preferred peptides to be conjugated to the dyes of the invention include, but are not limited to, neuropeptides, chemotactic peptides, cytokines (such as lymphokines), gastrointestinal peptides, toxins, protease substrates, synthetic peptides, experimental peptides, endothelin and protein kinase substrates. Protein conjugates of the invention include labeled enzymes, antibodies, catalytic antibodies, kinases, lectins, glycoproteins, histones, albumins, lipoproteins, avidin, streptavidin, protein A, protein G, phycobiliproteins, hormones, toxins and growth factors. Typically, the conjugated protein is an antibody, an antibody fragment, avidin, streptavidin, α-bungarotoxin, a lectin, growth factor or a phallotoxin.

In another embodiment of the invention, the conjugated substance ($S_C$) is a single nucleic acid base, single nucleoside, single nucleotide or a nucleic acid polymer. A nucleotide comprises an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference), an aminoallyl linkage (U.S. Pat. No. 4,711,955 to Ward et al. (1987), incorporated by reference) or other linkage. Nucleotides, as used herein, include natural and synthetic derivatives, including deoxynucleotides, dideoxynucleotides, cyclonucleotides and abasic nucleotide analogs, wherein the base is replaced by a fluorophore or hapten. Preferably, the conjugated nucleotide is a mono-, di- or triphosphate ester of an adenosine, a guanosine, a uridine, a cytidine or a thymidine. More preferably, the conjugated nucleotide is a nucleoside triphosphate or a deoxynucleoside triphosphate or a dideoxynucleoside triphosphate.

Preferred conjugates of nucleic acid polymers are labeled oligonucleotides composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Nucleic acid polymers are optionally single-stranded or multi-stranded; and may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids Such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether.

In another embodiment of the invention, the conjugated substance ($S_C$) is a carbohydrate, i.e. an organic compound composed of carbon, hydrogen and oxygen and occasionally nitrogen or sulfur, that include sugars, starches and celluloses. The conjugated substance is typically a polysaccharide, such as dextran, FICOL, heparin, glycogen, amylopectin, mannan, inulin, starch, agarose and cellulose, all of which are readily available. Preferred polysaccharide conjugates are dextran or FICOL conjugates, more preferably a dextran conjugate.

In another embodiment of the invention, the conjugated substance ($S_C$), is a lipid. Lipids are long-chain saturated or unsaturated aliphatic hydrocarbons (typically having 6–25 carbons) and their derivatives, such as fatty acids, alcohols, amines, amino alcohols, and aldehydes. The class of lipids includes glycolipids, phospholipids (for example, Compound 68 in Table 1) and sphingolipids. Alternatively, the conjugated substance is a lipid vesicle, such as a liposome, or is a lipoprotein. Alternatively, the dye contains a lipophilic substituent, e.g. where $R^4$ is a linear saturated or unsaturated fatty alkyl group, typically with 12–18 carbon atoms (for example Compounds 30, 31, and 53 in Table 1).

One class of conjugates of the present invention includes conjugates of biologically active molecules. Biologically active molecules include, but are not limited to, drugs, toxins, metabolites, pesticides, pollutants and the like. In one embodiment of the invention, the conjugated substance is a drug or toxin. Where the conjugated substance is a drug, preferred drugs of interest are the alkaloids (including morphine alkaloids), steroids, lactams having from 5 to 6 annular members, aminoalkylbenzenes, benzheterocyclics, purines, marijuana-derived drugs, vitamins, prostaglandins, antibiotics and aminoglycosides, as well as their individual derivatives and metabolites. Metabolites related to diseased states include spermine, galactose, phenylpyruvic acid and porphyrin Type 1. Among pesticides of interest are polyhalogenated biphenyls, phosphate esters, thiophosphates, carbamates, polyhalogenated sulfenainides, their metabolites and derivatives. In another embodiment, the conjugated substance is a tyramine derivative, and the resulting dye-conjugate is useful as a substrate for peroxidase enzymes (as described in U.S. Pat. No. 5,196,306 to Bobrow et al. (1993)).

The conjugated substance is optionally an ion-complexing moiety. Preferred ion-complexing moieties are crown ether, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995), U.S. Pat. No. 5,516,911 to London et al., and U.S. Pat. No. 5,049,673 to Tsien et al. (1991) (all incorporated by reference); derivatives of 2-carboxymethoxyaniline-N,N-diacetic acid (APTRA), as described by Ragu et al. AM. J. PHYSIOL. 256, C540 (1989); and pyridine- and phenanthroline-based metal ion chelators, as described in Copending application Ser. No. 08/384,945, filed Feb. 6, 1995 by Kuhn et al. (incorporated by reference). Preferably the conjugated ion-complexing moiety is a diaryldiaza crown ether chelator or a BAPTA chelator.

Conjugates of non-biological polymers are also useful aspects of the invention, including dye-conjugates of synthetic polymers, polymeric particles (including magnetic and non-magnetic microparticles) polymeric membranes, conducting and non-conducting metals and non-metals, and glass and plastic surfaces and particles. Conjugates are optionally prepared by copolymerization of a coumarin dye that contains an appropriate functionality (for example an acrylic acid- or styryl-substituent) while preparing the polymer, or more commonly by chemical modification of a polymer that contains functional groups with suitable chemical reactivity. In another embodiment of the invention, the conjugated substance is a glass or silica, which may be formed into an optical fiber or other structure. Other types of reactions that are useful for preparing dye-conjugates, especially of polymers, include catalyzed polymerizations or copolymerizations of alkenes, reactions of dienes with dienophiles, and transesterifications or transaminations. In another embodiment, the dyes of the invention are conjugated to a solid or semi-solid matrix. In yet another embodiment of the invention, a dye of the invention that is a substrate for an enzyme of interest is bound to a matrix that comprises a test strip or dipstick for the purpose of determining the presence of the enzyme of interest.

The preparation of dye conjugates using reactive dyes is well documented, e.g. by G. T. Hermanson, BIOCONJUGATE TECHNIQUES (Academic Press 1996); and R. Haugland, MOLECULAR PROBES HANDBOOK OF FLUORESCENT PROBES AND RESEARCH CHEMICALS, Sets 1–7 (1992); Brinkley et al., BIOCONJUGATE CHEM., 3, 2 (1992); Haugland et al., METH. MOL. BIOL. 45, 205 (1995)). Conjugates of the invention typically result from simply mixing the appropriate reactive dyes of the present invention and the substance to be conjugated in a suitable solvent in which both are soluble. The reaction preferably proceeds spontaneously without added reagents at room temperature or below. For those reactive dyes that are photoactivated, conjugation requires illumination of the reaction mixture to activate the reactive dye.

Preparation of conjugates of biological molecules typically comprises first dissolving the biomolecule to be conjugated in aqueous buffer at ~1–10 mg/mL at room temperature or below. Preferred buffers include carbonate buffers pH ~8.3 for reaction with succinimidyl esters, phosphate buffers pH ~7.2–8 for reaction with thiol-reactive functional groups and carbonate or borate buffers pH ~9 or above for reaction with isothiocyanates and dichlorotriazines. The appropriate reactive dye is then dissolved in water or a water-miscible solvent (usually DMSO or DMF) in an amount sufficient to give a suitable degree of conjugation when added to a solution of the biomolecule to be conjugated. Chemical modification of water-insoluble substances with reactive dyes of the invention, so that a desired dye-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive dyes to make them more readily soluble in organic solvents. Dyes that are sulfomethylated at $R^4$ are particularly useful as water-soluble reagents and typically enhance the water solubility of the fluorogenic substrates. The appropriate amount of dye is predetermined by experimentation in which variable amounts of the dye are added to the biomolecule and unconjugated dye is chromatographically removed (Example 38). An excess of dye is typically used, relative to the expected degree of dye substitution.

Figure 2:
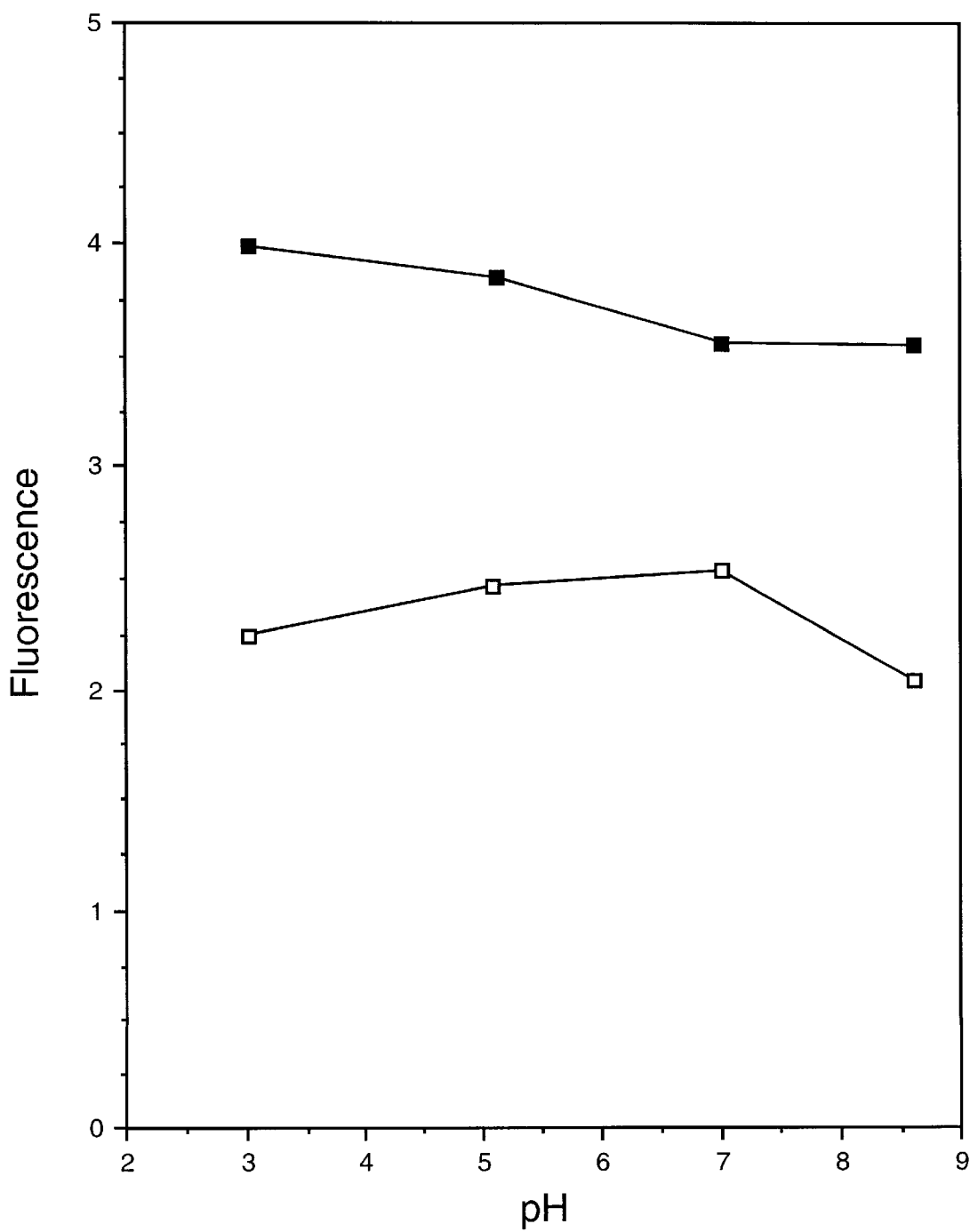
FIG. 2: A comparison of the pH-dependent fluorescence of goat-anti-mouse IgG antibody conjugates of 6,8-difluoro-7-hydroxy-4-methylcoumarin-3-acetic acid (Compound 11, ■) and 7-hydroxy-4-methylcoumarin-3-acetic acid (□).

Following addition of the reactive dye to the biomolecule, the solution is incubated for a suitable period (typically ~1 hour at room temperature to several hours on ice), the excess dye is removed by gel filtration, dialysis, HPLC, adsorption on an ion exchange or hydrophobic polymer or other suitable means. The dye-biomolecule conjugate is used in solution or lyophilized. The approximate degree of dye substitution is determined from the absorption of the dye-conjugate (Example 38) or by using the dry weight of the conjugate. The fluorescence can be measured as a function of degree of dye substitution (for instance as in Example 39 and FIGS. 2 and 3).

In one aspect of the invention, the conjugate of the invention is associated with an additional substance, that binds either to the fluorophore or the conjugated substance through noncovalent interaction. In a specific embodiment, the additional substance is an antibody to the dye, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

In another embodiment of the invention, one of the reactive dyes of the invention is provided in one or more suitable containers with instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

Dye Synthesis

The traditional chemistry for converting resorcinols to umbelliferone derivatives works well to prepare 6,8-difluoro-7-hydroxycoumarins. For example, the condensation of resorcinols with β-ketoesters such as ethyl acetoacetate in strongly acidic media via the widely general Pechmann reaction gives 4-methylumbelliferone derivatives (von Pechmann et al., CHEM. BER. 16, 2119 (1883); Sethna et al., ORG. REACT. 7, 1 (1953)). The utilization of 2,4-difluororesorcinol as a starting material produces 6,8-difluoro-7-hydroxy-4-methylumbelliferone.

It is possible to prepare 2,4-difluororesorcinol beginning with 2,3,4,5-tetrafluoronitrobenzene or a 2,4-alkoxy-substituted derivative. Two equivalents of alkoxide or benzyloxide are added, displacing the 2- and 4-fluorine atoms. The nitro group is then reduced via catalytic hydrogenation or chemical reduction, followed by diazotization and in situ reductive dediazonization using hypophosphorous acid (as in Example 3). Alternatively diazonium cations can be isolated pure as tetrafluoroborate or hexafluorophosphate salts, followed by reduction to the arene with sodium borohydride. Dealkylation with boron tribromide or another ether-cleaving reagent, or in the case of benzyl ethers, catalytic hydrogenolysis, then affords isomerically and constitutionally pure 2,4-difluororesorcinol (Example 4).

Substitution at the 4-position of the desired 6,8-difluoro-7-hydroxycoumarin is usually the result of substituents present in the ketone (or aldehyde) derivative that is condensed with the resorcinol. Examples include the condensation of ethyl 4-chloroacetoacetate with 6,8-difluororesorcinol (Example 27) or ethyl 4,4,4-trifluoroacetate with 6,8-difluororesorcinol (Example 19). However, certain coumarins in which $R^4$ is H can also be treated with inorganic cyanide followed by oxidation to yield 4-cyanocoumarins, thereby shifting the spectral properties of the dye to longer wavelengths (Hamprecht et al., (CA SELECTS: COLORANTS AND DYES 23, 125: 221838f (1996)).

It is known that reaction of 4-acylresorcinols with active methylene compounds under Knoevenagel condensation conditions gives 7-hydroxycoumarins substituted at the 3-position (Wolfbeis et al., CHEM. BER., 118, 3664 (1985) and references cited therein). For example, reaction of resorcylaldehyde with β-ketoesters gives 3-acyl derivatives, reaction with malonic acid esters gives 3-carboxy derivatives, which can be converted to 3-carboxyamides, reaction with malononitrile gives 3-cyano derivatives, which can be hydrolyzed to 3-carboxyamides and 3-carboxy derivatives, reaction with 3-acylacetic acids yields 3-acylcoumarins and reaction with aryl or heteroarylacetic acids gives 3-aryl or 3-heteroaryl derivatives.

The substitution of a 2,4-difluororesorcylaldehyde for resorcylaldehyde in these condensation reactions gives the corresponding 6,8-difluorocoumarin analogs. The required intermediate, 2,4-difluororesorcylaldehyde, which was previously unknown, is readily available by the modification of commercially available 2,3,4,5-tetrafluorobenzonitrile. Reaction of this benzonitrile with two equivalents of sodium methoxide results in the displacement of the ortho and para fluorine substituents with methoxide. The cyano group on the benzonitrile is then reduced to an aldehyde group using diisobutylaluminum hydride (DIBAL) under standard reduction conditions. The methoxy groups are then converted to hydroxides using boron tribromide in dichloromethane. Alternatively, 2,4-difluororesorcylaldehyde is obtained directly from 2,4-difluororesorcinol by treatment with mexamethylenetetraamine (Example 12).

3-Carboxy-substituted umbelliferones are readily converted to 3-heteroaryl substituted umbelliferones (as described in U.S. Pat. No. 3,014,041 to Hieusermann et al. (1961), incorporated by reference). For example, condensation of 7-hydroxycoumarin-3-carboxylic acid ethyl ester with o-aminothiophenols gives 3-(2'-benzothiazolyl)-7-hydroxycoumarins. The analogous 3-benzoxazoles and 3-benzimidazoles are prepared similarly from o-aminophenols or o-phenylenediamines, respectively. These synthetic strategies are applicable to the preparation of heteroaryl-substituted 6,8-difluoro-7-hydroxycoumarins, when applied to 6,8-difluoro-7-hydroxycoumarin-3-carboxylic acids. 3-Heteroaryl and 3-heteroacylcoumarins are additionally prepared starting from 3,5-difluoro-2,4-dihydroxybenzaldehyde and 3-heteroarylacetic acids or 3-heteroacylacetic acids (Example 16).

6,8-Difluorinated coumarins containing reactive groups at either $R^3$ or $R^4$ are typically prepared from preformed coumarins that contain functional groups such as carboxylates, sulfonates, or amines using methods well known in the art.

Substitution at the 3-position of umbelliferone compounds via electrophilic substitution is a general method for introduction of 3-substituents onto coumarins. For example 4-methylumbelliferone can be nitrated at the 3-position (Machida et al. CHEM. PHARM BULL, 23, 1385 (1975)) and formylated with the Vilsmeyer reagent. Additionally, 4-methylumbelliferone has been shown to react with aryldiazonium salts to give 3-aryl derivatives (U.S. Pat. No. 2,844,594 to Long et al. (1958); Sippel J. HISTOCHEMISTRY & CYTOCHEMISTRY, 29, 314 (1981)).

Any of the general synthetic schemes currently utilized for the preparation and derivatization of known 7-hydroxycoumarins are typically applicable to the preparation and derivatization of their 6,8-difluorinated analogs.

Applications and Method of Use

The dye compounds of the invention are generally utilized by combining a 6,8-difluorinated-7-hydroxycoumarin derivative described above with the sample of interest under conditions selected to yield a detectable optical response. The term "dye compound" is used herein to refer to all aspects of the claimed difluorinated coumarins, including reactive fluorinated coumarins, conjugates of fluorinated coumarins, lipophilic versions of fluorinated coumarins, and substituted fluorinated coumarins for use as enzyme substrates. The dye compound typically forms a covalent or non-covalent association or complex with an element of the sample, or is simply present within the bounds of the sample or portion of the sample. Optionally, the sample is washed to remove residual, excess or unbound dye compound. The sample is then illuminated at a wavelength selected to elicit the optical response. Typically, staining the sample is used to determine a specified characteristic of the sample by further comparing the optical response with a standard or expected response.

The fluorinated coumarin derivatives of the invention possess lower $pK_a$'s than their nonfluorinated analogs, resulting in a greater degree of deprotonation of the phenolic hydroxyl group at neutral pH and thus better solubility and fluorescence yield. For example, as shown in Table 3 the 6,8-difluorinated analog of 7-hydroxy-4-methylcoumarin possesses a higher quantum yield, lower $pK_a$ and greater resistance to photobleaching than the nonfluorinated dye under identical conditions. This $pK_a$ difference is particularly important in the preparation of protein conjugates with reactive versions of the dye, in that precipitation of the conjugate is minimized, even after labeling with multiple fluorophores, since the 7-hydroxy moiety is fully ionized at neutral pH. More unexpectedly, however, the fluorinated compounds of the invention are also inherently more fluorescent than other coumarins when both are fully deprotonated. The dye compounds are also unexpectedly more photostable.

TABLE 3

Spectral properties of selected dyes

| Dye | ε × 10⁻³ (cm⁻¹M⁻¹) | Absorbance (nm) | Emission (nm) | Quantum Yield (pH 9) | pK$_a$ | Photobleaching* |
|---|---|---|---|---|---|---|
| 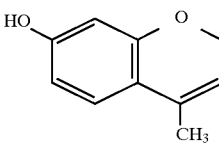 | 17 | 360 | 450 | 0.63 | 7.9 | 22% |
| 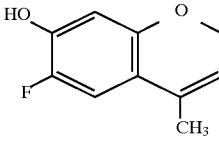 | 17.8 | 360 | 440 | 0.64 | 6.4 | 20% |
| 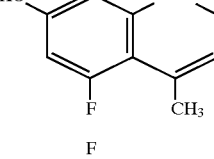 | 18.7 | 354 | 456 | 0.78 | 5.9 | 12% |
| 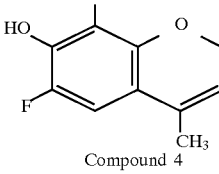  Compound 4 | 17.5 | 358 | 455 | 0.89 | 4.7 | 5% |
| 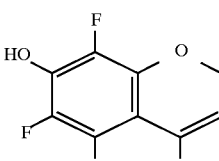 | — | 359 | 459 | 0.54 | 4.2 | — |
| 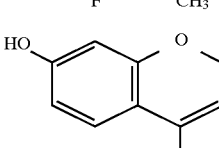 | 16 | 385 | 501 | 0.34 | 7.3 | 31% |
|  | 16 | 385 | 491 | 0.44 | 5.7 | 18% |
|   Compound 20 | 16.1 | 384 | 504 | 0.23 | 4.0 | 7% |

*Percent decrease in fluorescence intensity after 33 minutes of illumination in a fluorometer at the wavelength of maximum excitation.

For biological applications, the dye compounds of the invention are typically used in an aqueous or aqueous miscible solution prepared according to methods generally known in the art. The solubility of the dye compounds in aqueous solutions is substantially increased by selection of a dye that is substituted at $R^3$ by carboxy or carboxyalkyl, or substituted at $R^4$ by sulfomethyl. This is particularly desirable where $R^7$ is derived from a bulky and nonpolar moiety. The exact concentration of dye compound is dependent upon the experimental conditions and the desired results, but typically ranges from about one nanomolar to one millimolar or more. Concentrations of dye-conjugates that have utility as enzyme substrates are preferably above the Michaelis-Menton constant ($K_m$) of the enzyme that is being measured, which concentrations are typically in the micromolar to millimolar range. The optimal concentration is determined by systematic variation until satisfactory staining with minimal background fluorescence is accomplished.

The dye compound is combined with the sample in any way that facilitates contact between the dye compound and the sample components of interest. Typically the dye compound or a solution containing the dye compound is simply added to the sample. Lipohilic derivatives of the dye compound passively permeate through or into cellular membranes. Less cell-permeant embodiments of the invention are optionally physically inserted into cells, e.g. by pressure microinjection, scrape loading, patch clamp methods, or phagocytosis. Treatments that permeabilize the plasma membrane, such as electroporation, shock treatments or high extracellular ATP can also be used to introduce dye compounds into cells.

Dye compounds that possess a lipophilic substituent at $R^3$ or $R^4$ or that are conjugated to lipophilic molecules such as phospholipids will noncovalently incorporate into lipid assemblies, e.g. for use as probes for membrane structure or for incorporation in liposomes, lipoproteins, films, plastics, lipophilic microspheres or similar materials. Embodiments of the invention that have lipophilic moieties at either $R^3$ or $R^4$ and that are substrates for intracellular enzymes have enhanced penetration of the substrate into live cells and improved retention of the fluorescent product in the cells. Preferably the lipophilic moiety at $R^3$ or $R^4$ is a $C_{11}$ to $C_{18}$ alkyl substituent, and is more preferably at $R^4$.

Certain dye conjugates formed intracellularly are retained in cells or organelles through a period of time or sequence of events. In particular, haloalkyl- or halomethylbenzamide-substituted fluorinated coumarins (such as the chloromethylcoumarin galactoside, Compound 29 in Table 1 and Example 28) react with intracellular components such as glutathione, or retain the dye compounds within cells or within selected organelles, according to methods previously described (U.S. Pat. No. 5,362,628 to Haugland et al. (1994); U.S. Pat. No. 5,576,424 to Mao et al. (1996) (in cells); and U.S. Pat. No. 5,459,268 to Haugland et al. (1995) and copending application Ser. 08/383,298, filed Feb. 3, 1995 (in mitochondria); all incorporated by reference). Amine- and hydrazine-containing dyes permit fixation within cells using aldehyde-based fixatives such as formaldehyde and glutaraldehyde. Photoreactive dye compounds of the invention can selectively label external membranes of biological cells.

Alternatively, the dye compound is a conjugate of a specific binding pair member, and is used as a fluorescent probe for the complementary member of that specific binding pair, each specific binding pair member having an area on the surface or in a cavity which specifically binds to and is complementary with a particular spatial and polar organization of the other. Representative specific binding pairs are shown in Table 4. The dye compounds are useful as probes for a complementary binding pair member present in an animal cell, plant cell, bacteria, yeast or virus. Alternatively, the complementary member is immobilized on a solid or semi-solid surface, such as a polymer, polymeric membrane or polymeric particle (such as a polymeric bead). The dye-conjugate may also have an $R^7$ moiety that is enzyme cleaveable or photolabile.

TABLE 4

Representative Specific Binding Pairs

| antigen | antibody |
| --- | --- |
| biotin | avidin (or streptavidin or anti-biotin) |
| IgG* | protein A or protein G |
| drug | drug receptor |
| toxin | toxin receptor |
| carbohydrate | lectin or carbohydrate receptor |
| peptide | peptide receptor |
| protein | protein receptor |
| enzyme substrate | enzyme |
| DNA (RNA) | aDNA (aRNA)† |
| hormone | hormone receptor |
| ion | chelator |

*IgG is an immunoglobulin
†aDNA and aRNA are the antisense (complementary) strands used for hybridization The dye conjugates are used according to methods extensively known in the art; e.g. use of antibody conjugates in microscopy and immunofluorescent assays; and nucleotide or oligonucleotide conjugates for nucleic acid hybridization assays and nucleic acid sequencing (e.g., U.S. Pat. Nos. 5,332,666 to Prober, et al. (1994); 5,171,534 to Smith, et al. (1992); 4,997,928 to Hobbs (1991); and WO Appl. 94/05688 to Menchen, et al.; all incorporated by reference). In one embodiment, dye conjugates of the invention are simultaneously labeled with one or more additional dyes in an energy-transfer configuration, and analysis of the spectral properties of the conjugate indicates a mechanism or component of the sample. Alternatively, the dye-conjugate is simultaneously labeled with a hapten such as biotin or digoxigenin or other detectable label. Where the labeled specific binding pair member is a chelator of calcium, sodium, magnesium, potassium, or other biologically important metal ion, the dye-conjugate functions as an indicator of the ion, which indicators are optionally further conjugated to a biological or plastic polymer according to methods known in the art. The enhanced photostability and lower $pK_a$ of the dye compounds are particularly advantageous in use of the compounds for tracing. Biologically compatible polymers labeled with one or more fluorinated dyes are typically useful as tracers in biological systems. Examples of useful polymers include amino acid polymers (typically proteins, including fluorescent proteins), carbohydrate polymers (typically dextrans), and polymeric microspheres (typically polystyrene). The use of photolabile or "caged" conjugates permits the release of free dye in a sample with relatively precise temporal or spatial control.

The use of 6,8-difluorinated-7-hydroxycoumarins also results in improved fluorogenic enzyme substrates with the appropriate enzyme-cleavable substituent at $R^7$. Relative to their nonfluorinated counterparts, the substrates of the invention demonstrate increased fluorescence yield following the enzymatic reaction, not only from increased fluorescence of the reaction products, but in many cases from a higher rate of enzymatic turnover and resultant increased fluorescence yield. The 6,8-difluorinated hydroxycoumarin enzyme substrates are well suited to assess enzyme activity in a relatively acidic environment, e.g. detecting or quantifying acid phosphatase as well as alkaline phosphatase, or enzymes found in acidic organelles such as lysosomal glycosidases. Esterase substrates, where $R^7$ is derived from removal of a hydroxy from a carboxylic acid, serve as an indicator of cell viability and a as a substrate for certain esterases, such as lipases and cholinesterases.

The sample is optionally combined with one or more other solutions in the course of staining, including wash solutions, permeabilization and/or fixation solutions, and solutions containing additional detection reagents. Where the additional detection reagent has, or yields a product with, spectral properties that differ from those of the subject dye compounds, multi-color applications are possible. Dye compounds of the invention typically have bright blue to blue-green fluorescence (See Table 3) that contrasts well with reagents that give green, yellow, orange or red fluorescence.

At any time after or during staining, the sample is illuminated with a wavelength of light selected to give a detectable optical response, and observed with a means for detecting the optical response. Upon UV illumination, or illumination by laser sources that yield 2-photon UV excitation, the dye compounds display intense absorption as well as visible fluorescence emission. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The examples below are given so as to illustrate the practice of this invention. They are not intended to limit or define the entire scope of this invention.

EXAMPLES

Example 1
Preparation of 3,5-difluoro-2,4-dimethoxynitrobenzene (1):

Sodium methoxide (1.0M) is prepared by adding freshly cut sodium metal (rinsed with toluene) portionwise to anhydrous methanol (Aldrich Chemical Co.) under nitrogen in flame-dried glassware with stirring; an ice-water bath is used to control the reaction temperature. To 9.8 g (50 mmol) of 2,3,4,5-tetrafluoronitrobenzene (Aldrich) under nitrogen at room temperature in flame-dried glassware is added sodium methoxide solution (2.2 equivalents) via syringe over the course of 5–10 minutes, with stirring. The resulting reaction mixture is stirred at room temperature, while monitoring the progress of the reaction by thin layer chromatography (TLC). Additional sodium methoxide solution is added as necessary. Once the reaction reaches completion (1–24 hours), several drops of 1M citric acid are added, and the reaction mixture is partitioned between ether and water. The aqueous layer is extracted once with ether. The combined organic portions are washed once with brine, dried over anhydrous sodium sulfate, and concentrated under reduced pressure to give Compound 1 as 10.92 g (99%) of a pale yellow solid: m.p. 32.0°–32.5° C.; $^1$H NMR (CDCl$_3$) 7.52 (dd, 1H), 4.12 (s, 3H), 4.04 (s, 3H); $^{19}$F NMR (CDCl$_3$) 132.0 (m, 1F), 141.9 (d, 1F). Anal. calc. for $C_8H_7NO_4F_2$: C, 43.85; H, 3.22; N, 6.39. Found: C, 43.84; H, 3.15; N, 6.15.

Example 2
Preparation of 1-amino-3,5-difluoro-2,4-dimethoxybenzene (2):

The nitro group of 3,5-difluoro-2,4-dimethoxynitrobenzene (10.9 g, 49.7 mmol) is reduced by catalytic hydrogenation at 40 psi in ethanol/ethyl acetate over 10% Pd/carbon. Progress is monitored by TLC. When the reaction is complete, the catalyst is collected on a diatomaceous earth pad over a glass frit via filtration. The filtrate is concentrated in vacuo, giving pure 1-amino-3,5-difluoro2,4-dimethoxybenzene (2) as 9.40 g (99.8%) of a clear, pale brown oil: $^1$H NMR (CDCl$_3$) 6.25 (dd, 1H), 3.89 (two s, 6H), 3.7 (br s, 2H); $^{19}$F NMR (CDCl$_3$) 135.5 (d, 1F), 146.9 (s, 1F). Anal. calc. for $C_8H_9NO_2F_2$: C, 50.80; H, 4.80; N, 7.40. Found: C, 50.61; H, 4.81; N, 7.26. The hydrochloride salt is obtained by treating a dioxane solution of 5 with 4M HCl in dioxane, collecting the precipitate on a Buchner funnel, rinsing with dioxane, and drying in vacuo to give the hydrochloride salt of Compound 2 as a bone-white powder: m.p. 213°–218° C. (dec.); $^1$H NMR (D$_2$O) 7.1 (br d, 1H), 4.05 (br s, 6H); $^{19}$F (D$_2$O) 131.1 (dd, 1F), 141.6 (s, 1F). Anal. calc. for $C_8H_{10}NO_2F_2Cl$: C, 42.59; H, 4.47; N, 6.21. Found: C, 42.75; H, 4.47; N, 6.14.

Example 3
Preparation of 2,4-difluoro-1,3-dimethoxybenzene (3):

A 0.3M solution of Compound 2 (0.566 g, 2.99 mmol) in 4M HCl is chilled in an ice bath, and treated with a cold solution of sodium nitrite (1.05 equivalents) in water. The resulting diazonium salt solution is stirred for 15 minutes, and then hypophosphorous acid (50% aqueous solution, Aldrich, 20 equivalents) is added over 5 minutes. The resulting mixture is stirred at room temperature for two hours, then diluted with water. The resulting mixture is neutralized with aqueous sodium carbonate or sodium hydroxide, and extracted twice with ether. The organic extract is washed once with water, once with brine, and dried over anhydrous sodium sulfate. The solution is concentrated in vacuo and the resulting residue is purified by flash chromatography to give 0.38 g (73%) of Compound 3 as a clear, colorless liquid: $^1$H NMR (CDCl$_3$) 6.80 (td, 1H), 6.58 (m, 1H), 4.00 (s, 3H), 3.87 (s, 3H); $^{19}$F NMR (CDCl$_3$) 138.8 (d, 1F), 150.1 (d, 1F). Anal. calc. for $C_8H_8O_2F_2$: C, 55.19; H, 4.63. Found: C, 54.76; H, 4.63.

Alternatively, a 60 wt % solution of hydrogen hexafluorophosphate (0.88 mL) is added to a diazonium salt solution prepared from Compound 2 (0.57 g, 3.0 mmol) over two minutes, giving a brown precipitate. After standing at ice-bath temperature for 10 minutes, the precipitate is collected on a Buchner funnel, rinsed with water, air dried, and then dried in vacuo over $P_2O_5$/NaOH to give 0.72 g (70%) of a pale brown powder: m.p. 69°–72° C.; $^1$H NMR (CDCl$_3$) 8.00 (d, 1H), 4.42 (d, 3H), 4.38 (t, 3H); $^{19}$F NMR (CDCl$_3$) 128.5 (s, 1F), 144.6 (s, 1F). Anal. calc. for $C_8H_7N_2O_2PF_8$: C, 27.76; H, 2.04; Found: C, 27.83; H, 1.94; N, 8.23. To a brown solution of this diazonium hexafluorophosphate (0.71 g, 2.1 mmol) in 10 mL methanol under air at room temperature is added sodium borohydride (0.11 g, 3.0 mmol) portionwise over three minutes, resulting in vigorous gas evolution. The resulting pale yellow-red mixture is partitioned between ethyl ether and aqueous citric acid (0.25M).

The organic layer is washed once with brine, dried over anhydrous sodium sulfate, and concentrated to a pale brown oil. Flash chromatography provides 0.26 g (73%) of Compound 3 as a clear colorless liquid.

Example 4
Preparation of 2,4-difluororesorcinol (4):

A solution of Compound 3 (0.64 g, 3.7 mmol) in dichloromethane (0.3M, anhydrous) at room temperature under nitrogen is treated with boron tribromide solution (3.0 equivalents, 1.0M in dichloromethane, Aldrich or Fluka) via syringe over five minutes. The reaction is monitored by TLC, and takes 24–48 hours to reach completion; an additional 0.5 equivalents of boron tribromide solution is sometimes necessary to drive the reaction to completion. The reaction mixture is carefully quenched with water, and the resulting mixture is stirred until all precipitate dissolves. The resulting solution is extracted twice with ether. The ether extract is washed twice with brine, dried over anhydrous sodium sulfate, and concentrated under reduced pressure and purified by sublimation to yield 0.49 g (90%) of Compound 4 as a colorless crystalline solid: m.p. 100°–101° C.; $^1$H NMR (CDCl$_3$) 8.99 (s, 1H), 8.62 (s, 1H), 6.32 (td, 1H), 6.05 (m, 1H); $^{19}$F (CDCl$_3$) 145.4 (m, 1F), 156.0 (m, 1F). Anal. calc. for C$_6$H$_4$O$_2$F$_2$; C, 49.33; H, 2.76. Found: C, 48.96; H, 3.21; N, 0.028.

Example 5
Preparation of 6,8-difluoro-7-hydroxy-4-methylcoumarin (5):

A solution of 2,4-difluororesorcinol (Compound 4; 1.00 g, 8.76 mmol) and ethyl acetoacetate (1.14 g, 8.76 mmol) in 5 mL methanesulfonic acid is kept at room temperature for 24 hours, then poured into water (75 mL). The resulting precipitate is collected, rinsed with water and dried, giving 0.91 g of Compound 5 as a tan powder. An analytical sample is prepared by crystallization from light petroleum ether/methanol, giving the Compound 5 as colorless needles. UV-vis (pH 7 buffer): 358 nm, $\epsilon$=17,700 cm$^{-1}$M$^{-1}$; ex/em 358/452 nm. $^1$H NMR (CDCl$_3$) $\delta$7.12 (dd, 1H), 6.27 (s, 1H), 2.38 (s, 3H). $^{19}$F NMR (CDCl$_3$) $\Phi$ 136.5 (t, 1F), 152.8 (t, 1F).

Example 6
Preparation of the phosphatase substrate 6,8-difluoro-7-hydroxy-4-methylcoumarin phosphate, free acid (6):

To a solution of Compound 5 in pyridine under nitrogen at 0° C. is added a solution of POCl$_3$ (2 eq.) in pyridine. After the reaction is judged complete by TLC, the reaction is quenched by pouring the solution into crushed ice and neutralizing the mixture with ammonium hydroxide to pH 5. The pyridine is then extracted with chloroform, and the aqueous portion is lyophilized. The resulting crude product is purified by chromatography on SEPHADEX LH 20 resin, using water as eluant. The pure product fractions are pooled and lyophilized to yield a colorless solid. This solid is dissolved in water and stirred with DOWEX 50×4-200 strongly acidic cation exchange resin. The resin is removed by filtration and rinsed with water, and the combined filtrates are lyophilized to give Compound 6 as a nonfluorescent colorless solid.

Example 7
Preparation of the dealkylase substrate 6,8-difluoro-7-ethoxy-4-methylcoumarin (7):

A solution of Compound 5 (0.10 g, 0.47 mmol) and ethyl iodide (112 µL, 1.4 mmol) in acetone (10 mL) is stirred at reflux with potassium carbonate (207 mg, 1.5 mmol) for 72 hours, during which additional ethyl iodide (2×200 µL) is added at 24 and 48 hours. After cooling, the reaction mixture is filtered and the filtrate is concentrated to a colorless solid. This solid is purified by preparative TLC (silica gel, 1000 µm plate, eluting with ethyl acetate/hexanes 1:1) to give 50 mg of nonfluorescent Compound 7 as a colorless solid. UV-vis (MeCN): 298 nm, $\epsilon$=7,770 cm$^{-1}$M$^{-1}$; 279 nm, $\epsilon$=11,080 cm$^{-1}$M$^{-1}$. R$_f$(ethyl acetate/hexanes 3:2) 0.75. $^1$H NMR (CDCl$_3$) 7.10 (dd, 1H), 6.28 (s, 1H), 4.38 (q, 2H), 2.39 (s, 3H), 1.42 (t, 3H). $^{19}$F NMR (CDCl$_3$) 132.2 (t, 1F), 146.9 (d, 1F). Anal. calcd for C$_{12}$H$_{10}$O$_3$F$_2$: C, 60.00; H, 4.20; N, 0.00; Found: C, 59.98; H, 4.27; N, 0.01.

Example 8
Preparation of 6,8-difluoro-7-hydroxy-4-methylcoumarinyl β-D-galactopyranoside, tetraacetate (8):

A solution of NaOH (30 mg, 0.75 mmol) in 3 mL water is added to a solution of 6,8-difluoro-7-hydroxy-4-methylcoumarin (100 mg, 0.47 mmol), 2,3,4,6-tetra-O-acetyl-α-D-galactopyranosyl bromide (290 mg, 0.71 mmol), and tetrabutylammonium bromide (230 mg, 0.71 mmol) in 7 mL CH$_2$Cl$_2$. The reaction is stirred vigorously for 16 hours and poured into 50 ml water. The resulting product is extracted with CHCl$_3$ (50 mL×2), washed with brine (30 mL), dried over anhydrous MgSO$_4$, concentrated in vacuo, and chromatographed on silica gel (CHCl$_3$/MeOH 98:2) to yield 210 mg (82%) of 8. $^1$H-NMR (DMSO-d$_6$) $\delta$ 7.65 (dd, 1H), 6.50 (s, 1H), 5.42 (d, 1H), 5.33–5.20 (s+m, 3H), 4.29 (m, 1H), 4.06 (dm, 2H), 2.40 (s, 3H), 2.18 (s, 3H), 2.08 (s, 3H), 1.95 (s, 3H), 1.93 (s, 3H).

Example 9
Preparation of 6,8-difluoro-7-hydroxy-4-methylcoumarin, β-D-galactopyranoside (9):

A freshly prepared solution of NaOMe in dry MeOH (10 µL, 1N) is added to a solution of Compound 8 (70 mg, 0.13 mmol) in 3 mL dry MeOH. The reaction is stirred for 16 hours at 20° C., forming a colorless precipitate. The precipitate is then collected by filtration and washed with MeOH to yield 15 mg (31%) of Compound 9. The filtrate is combined with the wash solvent and treated with HRC resin, filtered, concentrated in vacuo, and chromatographed on SEPRADEX LH-20 resin, eluting with water to yield another 27 mg (55%) of Compound 9. $^1$H-NMR (DMSO-d$_6$) $\delta$ 7.60 (d, J=9.3 Hz, 1H), 6.47 (s, 1H), 5.31 (d, 1H), 4.98 (d, 1H), 4.87 (d, 1H), 4.55 (m, 1H), 4.49 (m, 1H), 3.69 (m, 1H), 3.60 (m, 1H), 3.50 (m, 1H), 3.4 (m, 3H), 2.40 (s, 3H). $^{19}$F-NMR (DMSO-d$_6$) $\Phi$ 126.40 (d, J=9.3 Hz, 1F), 142.30 (s, 1F).

Example 10
Preparation of 6,8-difluoro-7-hydroxy-4-methylcoumarin-3-acetic acid, ethyl ester (10). and 6,8-difluoro-7-hydroxy-4-methylcoumarin-3-acetic acid (11):

Diethyl acetylsuccinate (2.4 g, 11.1 mmol) is added to a solution of Compound 4 (1.3 g, 8.9 mmol) in 20 mL methanesulfonic acid at 20° C. The reaction is stirred for 16 hours and poured into 200 mL ice water. The product is extracted with EtOAc (80 mL×2), washed with brine (40 mL), dried over anhydrous MgSO$_4$, and concentrated in vacuo to yield a brown oil. The crude oil is purified by column chromatography on silica gel eluted with CHCl$_3$/MeOH (95:5 to 90:10) to yield 1.06 g (40%) of Compound 10 as an off-white solid. $^1$H-NMR (DMSO-d$_6$) $\delta$ 7.56 (d, 1H), 4.08 (q, 2H), 3.67 (s, 2H), 2.34 (s, 3H), 1.19 (t, 3H). $^{19}$F-NMR (DMSO-d$_6$) $\Phi$ 130.13 (t, 1F), 148.87 (d, 1F). Also isolated from the column is 0.50 g (20%) of 6,8-difluoro-7-hydroxy-4-methylcoumarin 3-acetic acid (Compound 11).

Example 11
Preparation of 6,8-difluoro-7-hydroxy-4-methylcoumarin-3-acetic acid, succinimidyl ester (12):

N-Trifluoroacetylsuccinimide (0.4 g, 1.9 mmol), which is prepared from N-hydroxysuccinimide and trifluoroacetic anhydride, is added to a solution of 11 (0.49 g, 1.8 mmol) in 5 mL dry pyridine. The reaction is stirred for 4 hours during which time more N-trifluoroacetyl succinimide (0.3 g×2) is added to force the reaction to completion. The reaction mixture is then poured into a 3% HCl solution (100 mL) and extracted with EtOAc (50 mL×2), washed with brine (30 mL), dried over anhydrous $MgSO_4$, and concentrated in vacuo to yield 0.95 g brown oil. The crude product is purified by column chromatography on silica gel, eluted with Hex/EtOAc/THF/HOAc (50:50:10:0.1 to 50:50:50:0.2 gradient) to yield 0.41 g (62%) of Compound 12 as a colorless solid. $^1$H-NMR (DMSO-$d_6$) δ 7.62 (d, 1H), 4.09 (s, 2H), 2.80 (s, 4H), 2.42, (s, 3H). $^{19}$F-NMR (DMSO-$d_6$) Φ 131.03 (t, 1F), 149.47 (d, 1F).

Example 12
Preparation of 3,5-difluoro-2,4-dihydroxybenzaldehyde (13):

A solution of 2,4-difluororesorcinol (0.50 g, 3.4 mmol) and hexamethylenetetraamine (0.96 g, 6.8 mmol) in 4 mL trifluoroacetic acid is heated to reflux for 24 hours. After cooling, the reaction is quenched by the addition of 2 mL 20% $H_2SO_4$, and then stirred for an additional hour. The reaction mixture is then poured into 50 mL water and extracted with EtOAc (50 mL×2), washed with brine (30 mL), dried over anhydrous $MgSO_4$, and concentrated in vacuo. The residue is purified by sublimation to yield 0.35 g (59%) of Compound 13 as a colorless powder. Mp. 141°–143° C. $^1$H-NMR (DMSO-$d_6$) δ 9.7 (s, 1H), 7.21 (dd, J=9.8; 6.5 Hz, 1H). $^{19}$F-NMR(DMSO-$d_6$) Φ 143.78 (t, J=9.8 Hz, 1F), 158.31 (d, J=6.5 Hz, 1F). Anal. calcd for $C_7H_4F_3O_3$: C, 48.29; H, 2.32. Found: C, 47.87, H, 2.62.

Example 13
Preparation of 6,8-difluoro-7-hydroxycoumarin-3-carboxylic acid, ethyl ester (14):

Diethyl manolate (264 mg, 2.0 mmol) is added to a solution of Compound 13 (90 mg, 0.5 mmol) in 5 mL methanesulfonic acid at 20° C. The reaction is stirred for 16 hours and poured into 50 mL ice water. The product is extracted with EtOAc (40 mL×2), washed with brine (20 mL), dried over anhydrous $MgSO_4$, and concentrated in vacuo to yield a brown oil. The crude oil is purified by column chromatography on silica gel eluting with $CHCl_3$/MeOH (95:5 to 90:10) to yield 102 mg (75%) of 14 as a yellowish-green powder: $^1$H-NMR (DMSO-$d_6$) δ 8.53 (s, 1H), 7.46 (d, J=11.0 Hz, 1H), 4.24 (q, J=8.2 Hz, 2H), 1.28 (t, J=8.1 Hz, 3H). $^{19}$F-NMR (DMSO-$d_6$) Φ 131.67 (t, J=11.2 Hz, 1F), 153.46 (br, 1F).

Example 14
Preparation of 6,8-difluoro-7-hydroxycoumarin 3-carboxylic acid (15):

A solution of 14 (100 mg, 0.37 mmol) and KOH (70 mg, 85%, 1.1 mmol) in 7 mL of THF/MeOH/$H_2O$ (5:5:1) is heated at 60° C. for 2 hours. The reaction is poured into 50 mL 5% HCl and extracted with EtOAc (40 mL×2), washed with brine (30 mL), dried over anhydrous $MgSO_4$, and concentrated in vacuo to yield 81 mg (94%) of Compound 15 as a green powder.

Example 15
Preparation of 6,8-difluoro-7-hydroxycoumarin-3-carboxylic acid, succinimidyl ester (16):

Succinimidyl trifluoroacetate (100 mg, 0.47 mmol), which is prepared from N-hydroxysuccinimide and trifluoroacetic anhydride, is added to a solution of Compound 15 (81 mg, 0.33 mmol) in 5 mL dry pyridine. The reaction is stirred for 4 hours with the addition of an additional 100 mg of succinimidyl trifluoroacetate to force the reaction to completion. The reaction mixture is then poured into a 3% HCl solution (50 mL) and extracted with EtOAc (50 mL×2), washed with brine (30 mL), dried over anhydrous $MgSO_4$, and concentrated in vacuo to yield 195 mg of a brown solid. The crude product is purified by column chromatography on silica gel eluting with Hex/EtOAc/THF/HOAc (50:50:10:0.1 to 50:50:50:0.2 gradient) to yield 100 mg (62%) of Compound 16 as a greenish powder.

Example 16
Preparation of 3-benzothiazolyl-6,8-difluoro-7-hydroxycoumarin (17):

A solution of Compound 13 (100 mg, 0.57 mmol) and benzothiazolyl-2-acetic acid, methyl ester (200 mg, 0.96 mmol) in 5 mL $CH_3SO_3H$ was heated at 60° C. for 16 hours. The reaction mixture is poured into 50 mL ice water and extracted with EtOAc (40 mL×2), washed with brine (30 mL), dried over anhydrous $MgSO_4$, and concentrated in vacuo. The residue is then purified by chromatography on silica gel to yield 140 mg (59%) of Compound 17. Abs. max: 425 nm; Em. max.: 492 nm; $\epsilon$=21,000 $cm^{-1}M^{-1}$ (pH 9.0 phosphate buffer, 50 mM). pKa=5.0.

Example 17
Preparation of 6,8-difluoro-7-hydroxy-4-methylcoumarinyl-β-D-glucuronic acid, methyl ester, triacetate (18):

A solution of NaOH (60 mg, 1.5 mmol) in 6 mL water is added to a solution of 6,8-difluoro-7-hydroxy-4-methylcoumarin (Compound 5, 100 mg, 0.47 mmol), bromo-2,3,4-tri-O-acetyl-α-D-glucopyranuronic acid methyl ester (320 mg, 0.80 mmol), and tetrabutylammonium bromide (230 mg, 0.71 mmol) in 14 mL $CH_2Cl_2$. The reaction is stirred vigorously for 16 hours and poured into 50 ml water. The product is extracted with $CHCl_3$ (50 mL×2), washed with brine (30 mL), dried over anhydrous $MgSO_4$, and concentrated in vacuo. The residue is chromatographed on silica gel ($CHCl_3$/MeOH 98:2) to yield 211 mg (85%) of Compound 18 as a colorless powder. $^1$H-NMR (DMSO$d_6$) δ 7.67 (d, 1H), 6.52 (s, 1H), 5.59 (d, 1H), 5.49 (t, 1H), 5.19 (t, 1H), 5.09 (t, 1H), 4.55 (d, 1H), 3.63 (s, 3H), 2.40 (s, 3H), 2.09 (s, 3H), 2.00 (two s, 6H). $^{19}$F-NMR (DMSO-$d_6$) Φ 127.34 (d, J=11.3 Hz, 1F), 142.09 (s, 1F).

Example 18
Preparation of 6,8-difluoro-7-hydroxy-4-methylcoumarinyl-β-D-glucuronide (19):

A solution of Compound 18 (105 mg, 0.20 mmol) and NaOH (20 mg, 0.5 mmol) in 5 mL of THF/MeOH/$H_2O$ (5:5:1) is stirred for 4 hours at 20° C. The reaction is neutralized by the addition of 42 μL of concentrated HCl diluted with 0.5 mL water. The organic solvent is removed and the aqueous residue is purified by chromatography on SEPHADEX LH-20 resin eluting with water to yield Compound 19.

Example 19
Preparation of 6,8-difluoro-7-hydroxy-4-trifluoromethylcoumarin (20):

A solution of Compound 4 (0.46 g, 3.1 mmol) and methyl-4,4,4-trifluoroacetoacetate (0.55 g, 3.2 mmol) in 7 mL CH$_3$SO$_3$H is stirred at 20° C. for 48 hours. The reaction mixture is poured into 70 mL ice water, and the resulting precipitate is collected by filtration, washed with water, dried in vacuo at 60° C. for 16 hours to yield 240 mg (30%) of Compound 20 as an off-white powder. $^1$H-NMR (DMSO-d$_6$) δ 7.33 (d, 1 H), 6.99 (s, 1H). $^{19}$F-NMR (DMSO-d$_6$) Φ 59.38 (s, 3F), 129.93 (t, J=9.9 Hz, 1H), 147.78 (d, J=9.3 Hz, 1F).

Example 20
Preparation of 6,8-difluoro-7-hydroxy-4-methylcoumarin-3-carboxylic acid ethyl ester β-D-glucuronic acid methyl ester triacetate (21):

A solution of 10% NaOH in water (1.5 eq) is added to a 0.1M solution of Compound 5 (1.0 eq) in CH$_2$Cl$_2$, followed by the addition of 1-bromo-2,3,4-tri-O-acetyl-α-D-glucopyranuronic acid methyl ester (1.6 eq) and tetrabutylammonium bromide (1.5 eq). The reaction mixture is stirred vigorously for 16 hours, then poured into 5 volumes of water. The product is extracted with CHCl$_3$ (2×), washed with brine, dried over anhydrous MgSO$_4$, and concentrated in vacuo. The residue is then purified by silica gel column chromatography (eluted with CHCl$_3$/MeOH) to yield Compound 21.

Example 21
Preparation of 6,8-difluoro-7-hydroxy-4-methylcoumarin-3-carboxylic acid β-D-glucuronide (22):

A 10% solution of NaOH in water (5.0 eq) is added to a 0.1M solution of Compound 21 in THF/MeOH (1:1). The reaction is stirred for 4 hours at 20° C. or until the reaction is complete as verified by TLC analysis. The reaction is neutralized by the addition of 1% HCl (5.2 eq) and concentrated in vacuo to remove the organic solvent. The aqueous residue is purified by chromatography on SEPHADEX LH-20 resin (eluted with water) to yield Compound 22.

Example 22
Preparation of 3,5-difluoro-2,4-dibenzyloxybenzaldehyde (23):

To a 0.1M solution of Compound 13 (1.0 eq) in acetone is added benzyl chloride (4.0 eq) and anhydrous K$_2$CO$_3$ (7.0 eq). The mixture is heated to reflux for 8 hours and filtered. The filtrate is concentrated in vacuo, and the residue is dissolved in EtOAc. The resulting solution is washed with 3% HCl, washed with brine, dried over anhydrous MgSO$_4$, and concentrated in vacuo. The residue is recrystallized from MeOH to yield Compound 23.

Example 23
Preparation of 1-(3,5-difluoro-2,4-dibenzyloxyphenyl) ethanol (24):

Methylmagnesium bromide (3.0M solution in ether, 1.1 eq) is added to a 0.4M solution of Compound 23 in ether (1.0 eq) at 0° C. The reaction is stirred at 0° C. for 1 hour, then warmed to 20° C. for an additional hour, and poured into 5 volumes of 1M citric acid solution. The resulting solution is extracted with ether (2×), washed with brine, dried over anhydrous MgSO$_4$, and concentrated in vacuo. The residue is purified by chromatography on silica gel (Hex/EtOAc) to yield Compound 24.

Example 24
Preparation of 3',5'-difluoro-2',4'-dibenzyloxyacetophenone (25):

A 1.0M solution of Compound 24 in CH$_2$Cl$_2$ is added to a suspension of pyridinium chlorochromate (4.0 eq) in CH$_2$Cl$_2$ at 20° C. with stirring. The reaction is stirred for 24 hours and filtered through a pad of diatomaceous earth. The filtrate is concentrated in vacuo and then purified by silica gel column chromatography (eluted with Hex/EtOAc) to yield Compound 25.

Example 25
Preparation of 3',5'-difluoro-2',4'-dihydroxyacetophenone (26):

A 0.4M solution of Compound 25 over 10% Pd/C (10% wt. to Compound 25) in EtOAc is hydrogenated at 40 psi for 24 hours. The reaction is filtered and concentrated in vacuo followed by sublimation to yield Compound 26.

Example 26
Preparation of 6,8-difluoro-7-hydroxy-4-methylcoumarin-3-carboxylic acid, ethyl ester (27):

A mixture of diethyl malonate (1.2 eq) in a 0.2M solution of Compound 26 in CH$_3$SO$_3$H is stirred at 20° C. for 24 hours. The reaction mixture is then poured into 7 volume of ice water and extracted with EtOAc (2×). The organic extract is then washed with brine, dried over anhydrous MgSO$_4$, and concentrated in vacuo. The residue is then purified by silica gel column chromatography (eluting with CHCl$_3$/MeOH) to yield Compound 27.

Example 27
Preparation of 4-chloromethyl-6,8-difluoro-7-hydroxycoumarin (28):

A solution of 2,4-difluororesorcinol (Compound 4, 0.20 g, 1.37 mmol) and ethyl 4-chloroacetoacetate (0.29 g, 1.75 mmol) in 2 mL methanesulfonic acid is kept at room temperature for 2.5 hours, then diluted with 25 mL water. The resulting precipitate is collected on a Büchner funnel and dried to give 134 mg of dimly fluorescent Compound 28 as a colorless powder. This product is purified further by chromatography (silica gel, ethyl acetate/hexanes): R$_f$=0.45 (EtOAc/hexanes 3:2); $^1$H NMR (CDCl$_3$-CD$_3$OD) δ 7.13 (dd, 1H), 6.41 (s, 1H), 4.52 (s, 2H); $^{19}$F NMR (CDCl$_3$-CD$_3$OD) Φ 136.38 (t, 1F), 153.26 (d, 1F).

Example 28
Preparation of the glycosidase substrate 4-chloromethyl-6,8-difluoro-7-hydroxycoumarin β-D-galactopyranoside (29):

A mixture of 4-chloromethyl-6,8-difluoro-7-hydroxycoumarin (Compound 28, 49 mg, 0.20 mmol), tetraacetobromogalactose (0.41 g, 1.0 mmol) and silver carbonate (275 mg, 1.0 mmol) in dichloromethane (10 mL) is stirred under nitrogen at room temperature for four hours. The reaction mixture is filtered and the filtrate concentrated in vacuo. The residue is purified by preparative TLC (silica gel, ethyl acetate/hexanes (1:1) as eluant) to give the non-fluorescent title compound, protected as its tetraacetate form, as 0.29 g of a colorless foam: R$_f$=0.38 (EtOAc/Hexanes 3:2). This foam is dissolved in anhydrous methanol (2.5 mL) under nitrogen at room temperature, and sodium methoxide solution (25 wt % in methanol, 43 μL, 0.20 mmol) is added. The resulting yellow solution is kept at room temperature for 30 minutes, then quenched by the addition of dilute aqueous citric acid. Concentration gives 0.25 g of a light yellow oil, which is purified by chromatography on lipophilic SEPHADEX LH-20 resin using 1:1 dioxane-water as eluant. The pure product fractions are pooled, then concentrated via rotary evaporation followed by lyophilization to give non-fluorescent Compound 29 as 80 mg of a colorless powder: R$_f$=0.65 (acetonitrile:water:acetic acid 90:5:5). $^1$H NMR (d$_6$-DMSO) δ 8.07 (s, 1H), 7.39 (d, 1H), 5.05 (m, 1H), 4.78 (d, 2H), 3.80 (s, 2H), 3.6 (m, integration obscured by solvent peak). $^{19}$F NMR (d$_6$-DMSO) Φ 126.78 (d, 1F), 144.61 (s, 1F).

Example 29
Preparation of 6,8-difluoro-4-heptadecyl-7-hydroxycoumarin (30):

A mixture of 2,4-difluororesorcinol (Compound 4, 0.15 g, 1.0 mmol) and ethyl stearoylacetate (354 mg, 1.03 mmol) in methanesulfonic acid (4 mL) is stirred at room temperature overnight. The reaction mixture is partitioned between ethyl acetate and water. The ethyl acetate layer is washed with brine (1×) and dried over sodium sulfate, then concentrated to 0.67 g of a pale brown solid, which is purified by silica gel chromatography to give 49 mg of Compound 30 as a colorless powder: $R_f$=0.64 (EtOAc/hexanes 3:2). $^1$H NMR ($CDCl_3$) δ 7.12 (dd, 1H), 6.22 (s, 1H), 1.7–0.7 (m, 70H). $^{19}$F NMR ($CDCl_3$) Φ 139.8 (t, 1F), 153.5 (d, 1F).

Example 30
Preparation of the glycosidase substrate 6,8-difluoro-4-heptadecyl-7-hydroxycoumarinyl β-D-galactopyranoside (31):

A mixture of 6,8-difluoro-4-heptadecyl-7-hydroxycoumarin (Compound 30, 27 mg, 0.062 mmol), tetraacetobromogalactose (127 mg, 0.31 mmol), and silver carbonate (85 mg, 0.31 mmol) in dichloromethane (6 mL, anhydrous) is stirred under nitrogen at room temperature overnight. The reaction mixture is filtered; concentration of the filtrate gives 0.20 g of an oil, which is purified by preparative silica gel TLC (EtOAc/hexanes 1:1) to give the nonfluorescent tetraacetate of Compound 31 as 29 mg of a colorless solid: $R_f$=0.0.72 (EtOAc/hexanes 3:2). All of this solid (0.038 mmol) is then dissolved in anhydrous methanol (2.5 mL), and sodium methoxide solution (25 wt % in methanol, 9 μL, 0.04 mmol) is added. After 30 minutes the reaction is quenched by the addition of dilute aqueous citric acid, followed by concentration in vacuo. The residue is then purified by chromatography on lipophilic SEPHADEX LH-20 resin, using 1:1 water:dioxane as eluant. The product fractions are pooled and concentrated via rotary evaporation then lyophilization to give Compound 31 as 40 mg of a colorless and nonfluorescent solid: $R_f$=0.83 (acetonitrile:water:acetic acid 90:5:5).

Example 31
Preparation of 3-(4-aminophenyl)-6,8-difluoro-7-hydroxy-4-methylcoumarin (33):

An adapted methodology of U.S. Pat. No. 2,844,594 to Sidney et al. (1958) is utilized. To a solution of 4-nitroaniline (69 mg, 0.50 mmol) in 3M HCl (3 mL) under air in an ice bath is added solid sodium nitrite (38 mg, 0.55 mmol). The resulting diazonium salt solution is kept cold. Meanwhile, to a solution of 6,8-difluoro-7-hydroxy-4-methylcoumarin (Compound 5, 0.10 g, 0.47 mmol) in acetone (3 mL) is added sodium acetate (0.11 g), followed by a solution of cuprous bromide (30 mg) in 1 mL water. To the resulting brownish mixture at room temperature is added the cold diazonium salt solution with stirring. Gas evolution is observed. The resulting brown-amber solution is kept at room temperature overnight, then partitioned between ethyl acetate and water. The organic layer is washed with brine (1×), dried over sodium sulfate, and concentrated to give 0.18 g of an amber oil, which is purified by chromatography on silica gel (EtOAc/hexanes) to give nonfluorescent 6-difluoro-7-hydroxy-4-methyl-3-(4-nitrophenyl)coumarin (Compound 32) as 27 mg of a light brown oil ($R_f$=0.17 EtOAc:hexanes 3:2); $^1$H NMR ($CD_3OD$) δ 8.31 (d, 2H), 7.59 (d, 2H), 7.38 (d, 1H), 2.25 (s, 3H). $^{19}$F NMR ($CD_3OD$) Φ 136.1 (t, 1F), 155.5 (d, 1F).

To a pale yellow solution of Compound 32 (23 mg, 0.069 mmol) in ethyl acetate/ethanol (2:1, 3 mL) is added stannous chloride dihydrate (78 mg, 0.35 mmol). The resulting solution is heated at reflux for 12 hours, then diluted with ethyl acetate. The resulting solution is washed with saturated aqueous sodium bicarbonate, brine, and dried over sodium sulfate. The pH of the aqueous layer is adjusted from approximately 9 to approximately 1, followed by additional extraction of the solution with ethyl acetate. The combined extracts are concentrated to give 23 mg of a pale yellow powder, which is then purified by preparative silica gel TLC, using chloroform:methanol:acetic acid (50:5:1) as eluant. Compound 33 is obtained as 8 mg of pale yellow powder: $R_f$=0.44 chloroform:methanol:acetic acid (50:5:1). $^1$H NMR ($d_6$-DMSO) δ 7.0 (br s, 1H), 6.88 (d, 2H), 6.55 (d, 2H), 5.1 (br s, 2H (NH)), 2.14 (s, 3H).

Example 32
Preparation of 6,8-difluoro-4,7-dihydroxycoumarin (34):

A solution of 2,4-difluororesorcinol (Compound 4, 0.20 g, 1.5 mmol) and diethylmalonate (0.28 g, 1.75 mmol) in methanesulfonic acid (2 mL) is heated at 110° C. for two days, then cooled and partitioned between ethyl acetate and water. The organic layer is washed with brine (1×) and dried over sodium sulfate, then concentrated to give 0.52 g of a brown oil, which is purified by silica gel chromatograpy using chloroform/methanol/acetic acid (50:5:1) as eluant to give 18 mg of Compound 34 a pale brown powder: $R_f$=0.23 (chloroform/methanol/acetic acid (20:4:1). $^1$H NMR ($d_6$-DMSO) δ 7.30 (br s, 1H), 4.88 (br s, 1H). $^{19}$F NMR ($d_6$-DMSO) Φ 134.0 (s, 1F), 149.7 (s, 1F).

Example 33
Preparation of the fluorogenic guanidinobenzoatase substrate 6,8-difluoro-7-hydroxy-4-methylcoumarinyl p-guanidinobenzoate (35):

To a pale yellow solution of 6,8-difluoro-7-hydroxy-4-methylcoumarin (Compound 5, 0.13 g, 0.61 mmol) in THF (5 mL) under air at room temperature is added a solution of 4-guanidinobenzoic acid hydrochloride (132 mg, 0.61 mmol) in 4 mL water, followed by 1-(3-dimethylaminopropyl)-3-ethylcarbodiimide hydrochloride (EDC; 125 mg, 0.65 mmol). The resulting solution is stirred at room temperature overnight, followed by the addition of more EDC (100 mg). After two hours, TLC analysis indicates the starting materials are consumed. Volatiles are removed in vacuo, and a portion of the residue (0.61 g of pale yellow powder) is purified by chromatography on SEPHADEX LH-20 resin using water:dioxane (1:1) as eluant to give nonfluorescent Compound 35 as a colorless powder: $R_f$=0.30 ($MeCN:H_2O:AcOH$ 90:5:5). Upon treatment with ammonia vapor, a TLC spot corresponding to Compound 35 becomes blue fluorescent.

Example 34
Preparation of a caged version, 6,8-difluoro-O-(4,5-dimethoxy-2-nitrobenzyl)-7-hydroxy-4-methylcoumarin (36):

To a solution of 6,8-difluoro-7-hydroxy-4-methylcoumarin (Compound 5) in dichloromethane (0.5M) is added 1.1 eq 4,5-dimethoxy-2-nitrobenzyl bromide and 1.1 eq silver carbonate. The resulting mixture is stirred at room temperature until TLC analysis shows consumption of all starting dye. The reaction mixture is filtered, and the retentate is washed with dichloromethane. The concentrated filtrate is purified by silica gel chromatography using EtOAc/hexanes to give non-fluorescent Compound 36 as a colorless powder. Photolysis with UV irradiation regenerates fluorescent 6,8-difluoro-7-hydroxy-4-methylcoumarin.

Example 35
Preparation of the glycosidase substrate 6,8-difluoro-7-hydroxy-4-sulfomethylcoumarinyl β-D-galactopyranoside sodium salt (39):

To a solution of dimly fluorescent 4-chloromethyl-6,8-difluoro-7-hydroxycoumarin (Compound 28, 50 mg, 0.20 mmol) in 4 mL ethanol is added a solution of sodium sulfite (29 mg, 0.23 mmol) in 1 mL water. The resulting yellow mixture is heated at reflux for 24 hours, then cooled and filtered. The resulting yellow mixture is heated at reflux for 24 hours, then cooled and filtered. The filtrate is concentrated and the brightly fluorescent product, 6,8-difluoro-7-hydroxy-4-sulfomethylcoumarin, sodium salt (Compound 37) is purified by chromatography on SEPHADEX LH-20 resin using water as eluant. On TLC the $R_f$ of the starting is dye is 0.85, whereas the $R_f$ of the reaction product is 0.10 (chloroform:methanol:acetic acid 15:3:1). $^1$H NMR (D$_2$O) δ 7.35 (d, 1H), 6.21 (s, 1H), 4.32 (s, 2H). $^{19}$F NMR (D$_2$O) Φ 134.8 (t, 1F), 157.7 (d, 1F).

To a 0.5M solution of 6,8-difluoro-7-hydroxy-4-sulfomethylcoumarin sodium salt in dichloromethane:dioxane (1:1) is added 5 molar equivalents of tetraacetobromogalactose and 5 molar equivalents of silver carbonate. The resulting mixture is stirred at room temperature until TLC indicates consumption of the starting dye. The reaction mixture is filtered and the filtrate concentrated to a residue that is purified by preparative silica gel TLC using methanol/chloroform as eluant to give a nonfluorescent reaction product, i.e. Compound 38 in protected form as the tetraacetate, as a colorless powder.

To a 0.5M solution of 6,8-difluoro-7-hydroxy-4-sulfomethylcoumarinyl β-D-galactopyranoside tetraacetate in methanol is added one molar equivalent of sodium methoxide as a 25 wt % solution in methanol. The resulting solution is stirred at room temperature for one hour, then neutralized by adding dilute aqueous citric acid. The reaction mixture is concentrated, and the residue is purified by chromatography on SEPHADEX LH-20 resin using water as eluant. The product fractions are combined and lyophilized to give Compound 39 as a non-fluorescent colorless powder.

Example 36

Preparation of a nucleotide conjugate of 6,8-difluoro-7-hydroxy-4-methylcoumarin-3-acetic acid, succinimidyl ester:

To a solution of 2 mg of 5-(3-aminoallyl)-2'-deoxyuridine-5'-triphosphate, ammonium salt (Sigma Chemical) in 100 μL of water is added a solution of 3 mg of Compound 12 (Example 11) in 100 μL of DMF, followed by addition of 5 μL of triethylamine. After the mixture is stirred at room temperature for 3 hours, the solution is evaporated to dryness under vacuum and the residue is purified by chromatography over lipophilic SEPHADEX resin using water for elution. The first blue fluorescent fractions are combined and lyophilized to give the fluorescent nucleotide conjugate as a colorless solid (Compound 40)

Alternatively a fluorescent conjugate (Compound 41) of deoxyuridine-5'-triphosphate is prepared using 5-(3-amino-1-propynyl)-2'-deoxyuridine-5'-triphosphate in place of 5-(3-aminoallyl)-2'-deoxyuridine-5'-triphosphate (as described in Hobbs, Jr. et al, supra).

Example 37

Preparation of an oligonucleotide conjugate of 6,8-difluoro-7-hydroxy-4-methylcoumarin-3-acetic acid (Compound 42):

A sample of 500 μg of a 5'-amine modified, 24-base M13 primer sequence is dissolved in 220 μL 0.1M NaHCO$_3$, pH 8.5. To this is added 1 mg of Compound 12 (Example 11) in 35 μL of DMF. After 16 hours at room temperature, 15 μL of 5M NaCl and 3 volumes of cold 100% ethanol are added. The resulting mixture is cooled to −20° C., centrifuged, and the ethanol supernate is decanted. The pellet is briefly rinsed and dissolved in 100 μL H$_2$O. The labeled oligonucleotide is purified by HPLC on a 300 Å C8 reverse phase column using a ramp gradient of 0.1M triethylammonium acetate (pH ~7) and acetonitrile (15→60% over 30 min). The desired peak is collected and evaporated to give the fluorescent oligonucleotide (Compound 42).

Example 38

Protein conjugates of 6,8-difluoro-7-hydroxy coumarins:

A series of dye conjugates of immunoglobulin G (IgG), goat anti-mouse antibody (GAM) or what germ agglutinin (WGA) are prepared separately using the reactive dyes 6,8-difluoro-7-hydroxy-4-methylcoumarin-3-acetic acid, succinimidyl ester (Compound 12), 6,8-difluoro-7-hydroxycoumarin-3-carboxylic acid, succinimidyl ester (Compound 16, Example 15), 7-hydroxy-3-carboxycoumarin, succinimidyl ester, and 7-hydroxy-4-methylcoumarin-3-acetic acid, succinimidyl ester, as follows:

A fresh solution of the desired protein is prepared at 10 mg/mL in 0.1M sodium bicarbonate. The desired labeling reagent is dissolved in DMF to give a concentration of 10 mg/mL. A predetermined amount of the labeling reagent is slowly added to the protein solution with stirring. A molar ratio of 10 equivalents of dye to equivalent of protein is typical, though the optimal amount varies with the particular labeling reagent and the protein being labeled. The reaction mixture is incubated at room temperature for one hour, or on ice for several hours. The dye-protein conjugate is separated from free unreacted reagent by size exclusion chromatography on a CELLUFINE GH-25 column equilibrated with PBS. The initial, protein-containing colored band is collected from the column and the degree of labeling is determined by measuring the absorbance at the absorbance maximum of each fluorophore, using an extinction coefficient of 18,000 cm$^{-1}$M$^{-1}$ for each coumarin. The protein concentration is determined by reading at 280 nm and by correcting the value by the percentage of the dye absorption at the same wavelength.

| | | Degree of Substitution | | | |
|---|---|---|---|---|---|
| Protein | Molar Ratio (dye:protein) | 7-hydroxy-4-methylcoumarin-3-acetic acid, SE | Compound 12 | 7-hydroxycoumarin-3-carboxylic acid, SE | Compound 16 |
| IgG | 5 | 3.2 | 4.4 | — | — |
| IgG | 10 | 6.2 | 5.5 | — | — |
| IgG | 15 | 7.1 | 7.6 | — | — |
| GAM | 5 | 3.4 | 4.5 | 2.8 | 1.1 |
| GAM | 10 | 7.1 | 6.9 | 5.4 | 2.4 |
| GAM | 15 | 9.9 | 10.5 | — | — |

-continued

| Protein | Molar Ratio (dye:protein) | Degree of Substitution | | | |
|---|---|---|---|---|---|
| | | 7-hydroxy-4-methylcoumarin-3-acetic acid, SE | Compound 12 | 7-hydroxycoumarin-3-carboxylic acid, SE | Compound 16 |
| GAM | 20 | — | — | 7.9 | 4.4 |
| WGA | 5 | — | 4.2 | — | — |
| WGA | 10 | — | 6.7 | — | — |
| WGA | 15 | — | 9.3 | — | — |

Figure 3:
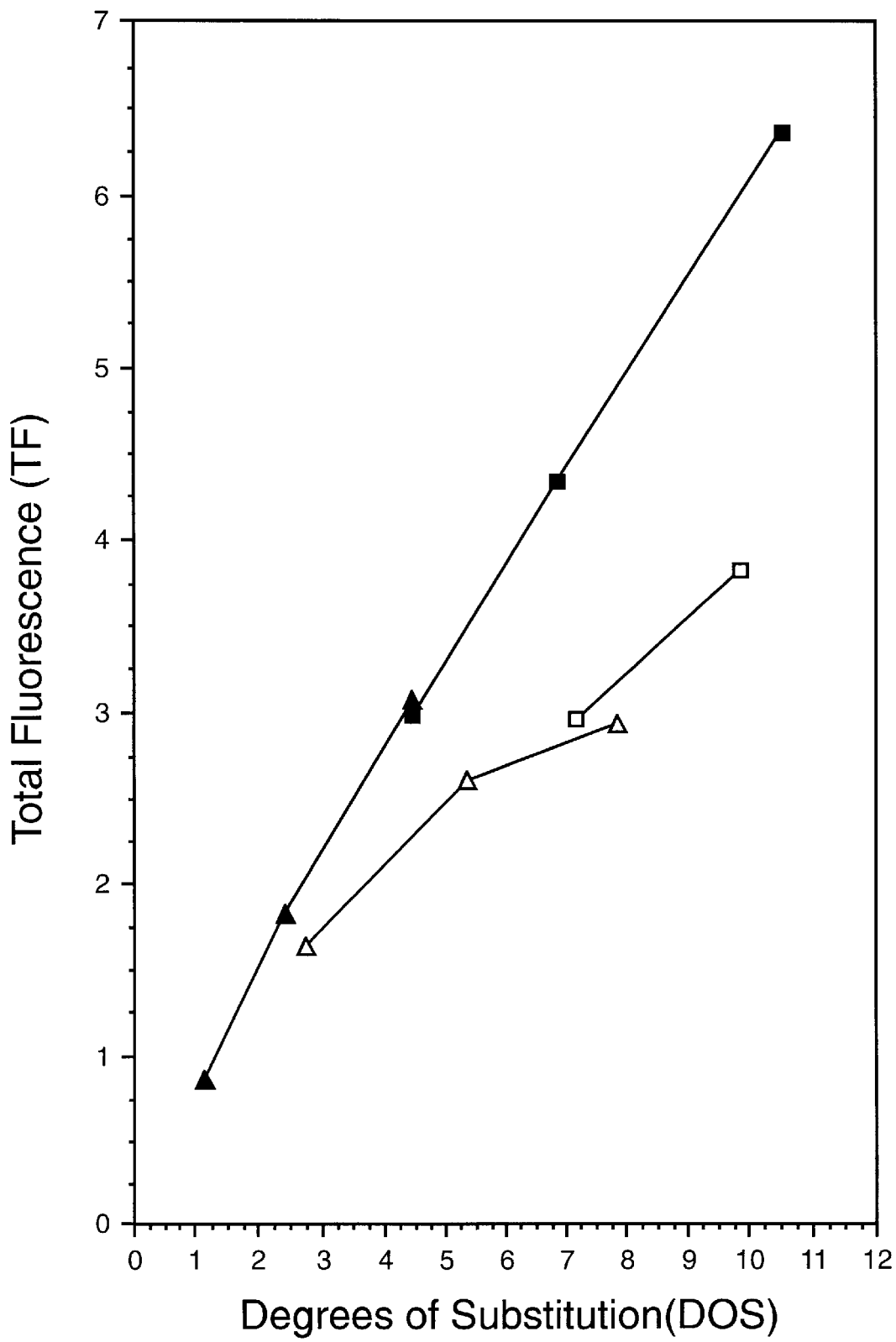
FIG. 3: Total fluorescence of selected goat-anti-mouse IgG antibody conjugates of fluorinated dyes of the invention compared to their nonfluorinated analogs: 6,8-difluoro-7-hydroxy-4-methylcoumarin-3-acetic acid, succinimidyl ester (Compound 12, ▲), 7-hydroxy-4-methylcoumarin-3-acetic acid, succinimidyl ester (Δ), 6,8-difluoro-7-hydroxy-3-carboxycoumarin, succinimidyl ester (Compound 16, ■), and 7-hydroxycoumarin-3-carboxylic acid, succinimidyl ester (□), as described in Example 39.

Example 39
Total fluorescence of selected dye-protein conjugates as a function of degree of substitution:

A series of goat anti-mouse IgG conjugates is prepared using the reactive dyes 6,8-difluoro-7-hydroxy-4-methylcoumarin-3-acetic acid, succinimidyl ester (Compound 12), 6,8-difluoro-7-hydroxycoumarin-3-carboxylic acid, succinimidyl ester (Compound 16)), 7-hydroxycoumarin-3-carboxylic acid, succinimidyl ester, and 7-hydroxy-4-methylcoumarin-3-acetic acid, succinimidyl ester so as to yield derivatives with similar degrees of substitution. Fluorescence of the conjugates of the fluorinated coumarins is higher than that of the analogous non-fluorinated coumarins, as shown in FIG. 3.

Example 40
Preparation of aminodextran conjugates of fluorinated coumarins:

70,000 MW aminodextran (50 mg) that is derivatized with an average of 13 amino groups, is dissolved in 0.1M NaHCO$_3$ to give a concentration of 10 mg/mL. A succinimidyl ester derivative of the desired fluorinated dye is added in an amount sufficient to give dye/dextran ratio of 12. After 6 hours at room temperature, the conjugate is purified on SEPHADEX G-50 resin eluting with water and the product is lyophilized. Typically ~6 moles of dye are conjugated to 70,000 g dextran.

Example 41
Preparation of fluorescent dye-labeled microspheres:
Method A
1.0 μm uniform amine-derivatized polystyrene microspheres are suspended at ~2% solids in 100 mM bicarbonate buffer pH 8.3 and treated with 2 mg/mL of an amine-reactive fluorinated dye such as a succinimidyl ester derivative (for example, Compound 12). After 1 hour the microspheres are separated by centrifugation and washed with buffer.
Method B
Carboxylate-modified microspheres are suspended in a solution of a protein that has been conjugated to a fluorinated dye (prepared as in Example 38). Excess protein is removed by centrifugation and washing. Microparticles of a size that cannot be centrifuged are separated from protein by dialysis through a semi-permeable membrane with a high MW cutoff or by gel filtration chromatography.
Method C
A protein that has been conjugated to a fluorinated dye (Example 38) is covalently coupled through its amine residues to the carboxylate groups of the polymer using ethyl 3-(dimethylaminopropyl)carbodiimide (EDAC).
Method D
Biotinylated microspheres (Molecular Probes, Inc) are treated with a streptavidin, avidin or anti-biotin conjugate of a 6,8-difluorinated coumarin dye and the conjugates are isolated as in Method B. The larger particles are analyzed for uniformity of staining and brightness using flow cytometry and are useful as standards for microscopy and flow cytometry as well as detection reagents.

Example 42
Utility of protein conjugates as immunoreagents:
Antibody conjugates of the succinimidyl esters of 6,8-difluoro-4-methylcoumarin-3-acetic acid (Compound 12), 6,8-difluoro-7-hydroxycoumarin-3-carboxylic acid (Compound 16), 7-hydroxy-4-methylcoumarin-3-acetic acid, and 7-hydroxycoumarin-3-carboxylic acid are prepared with degrees of substitution of approximately 4–6. INOVA slides are rehydrated in 1% bovine serum albumin (BSA) in phosphate buffered saline (PBS) for 30 minutes. The slide is drained thoroughly. Human autoantibody is applied and the slide is incubated 30 minutes then rinsed thoroughly in PBS. Mouse anti-human antibody is applied and the slide is incubated 30 minutes then rinsed thoroughly in PBS. Each blue fluorescent goat anti-mouse antibody conjugate is applied as a solution that is 10 μg/mL, diluted in 1% BSA/PBS. The slides are incubated for 30 minutes. The labeled slides are then rinsed thoroughly in PBS, then rinsed in 50 mM Tris pH 8.0, mounted in 50 mM Tris pH 8.0, and viewed through a longpass coumarin filter. All samples give predominantly nuclear staining. One image of the slide is acquired every 5 seconds for 100 seconds with continuous illumination of the specimen, using a coumarin longpass filter.

Example 43
Preparing a DNA hybridization probe using fluorescent nucleotide conjugates:

For each labeling reaction, a microfuge tube containing about 1 μg of a ~700 bp Hind III-Bgl II fragment of the E. coli lacZ structural gene is heated for ~10 minutes at 95° C. to fully separate the strands. The DNA is immediately cooled on ice, to prevent the strands from reannealing. To the DNA mixture on ice is added 2 μL of a 2 mg/mL mixture of random sequence hexanucleotides, in 0.5M Tris-HCl, pH 7.2, 0.1M MgCl$_2$, 1 mM dithiothreitol; 2 μL of a dNTP labeling mixture (1mM dATP, 1 mM dGTP, 1 mM dCTP, 0.65 mM dTTP and 0.35 mM either Compound 40 or Compound 41 (Example 36). Sterile distilled, deionized water is added to bring the total volume of each sample to 19 μL. A 1 μL volume of Klenow DNA polymerase (2 units/μL) is added carefully to the samples and they are mixed by pipetting up and down repeatedly. The samples are incubated for one hour at 37° C. The reactions are stopped by adding 2 μL of 0.2M EDTA, pH 8.0. The labeled DNA is precipitated by addition of 2.5 μL of 4M LiCl and 75 μL prechilled (−20° C.) 100% ethanol and mixing well. Precipitation is allowed to continue for 2 hours at −20° C. and the nucleic acids are then recovered by centrifugation at 12,000 rpm in a microfuge. The pellets are washed briefly with cold 70% ethanol, then with cold 100% ethanol. The pellets are dried briefly and dissolved in 10 mM Tris-HCl, pH 8.0, 1 mM EDTA. A portion consisting of 1/10 to 1/2 of each sample is analyzed by gel electrophoresis on a 1% agarose minigel under standard conditions. The labeled DNA products are suitable for in situ hybridization experiments for the detection of RNA or DNA, such as is associated with the *E. coli* lacZ gene in cells or tissues.

Example 44

Incorporation of fluorescent nucleotide conjugates into DNA amplification products:

A DNA amplification reaction is prepared as follows. 1 μL each of 20 μM solutions of two oligonucleotide primers that hybridize to the human β-actin gene (Human β-Actin Control Amplimer Set, CLONTECH Laboratories, Inc, Palo Alto, Calif.) are added to a labeling reaction containing 5 μL DNA template (100 pmol of a plasmid containing the entire gene), 5 μL 10× reaction buffer (100 mM Tris, pH 8.3, 500 mM KCl), 2.5 μL 1 mM Compound 40 (fluorescent dUTP), 1 μL 10 mM dATP, 1 μL 10 mM dCTP, 1 μL 10 mM dGTP, 1.5 μL 5 mM dTTP, 3 L 25 mM MgCl$_2$, and 28 μL distilled, deionized water. The sample is transferred to a commercially available thermocycler and processed according to the following program: one cycle, 94° C., 2.5 minutes; 30 cycles, 94° C., 1 minute, 50° C. 1 minute, 72° C., 1 minute; one cycle, 72° C., 5 minutes; then 4° C. overnight. An aliquot consisting of 10% of the sample (5 μL) is mixed with an equal volume of 10% glycerol and loaded onto a 0.9% agarose minigel. Samples are electrophoresed until the bromophenol blue in size markers in an adjacent gel migrates at least half of the length of the gel. Blue fluorescent bands of the expected size are visible when the gel is illuminated with 300 nm ultraviolet light, as is a diffuse band containing unincorporated dUTP conjugate.

Example 45

In situ hybridization of an RNA probe prepared using fluorescent nucleotide conjugates:

Mouse fibroblasts are fixed and prepared for mRNA in situ hybridization using standard procedures. A fluorophore-labeled RNA probe is prepared by in vitro transcription of a plasmid containing the mouse actin structural gene cloned downstream of a phage T3 RNA polymerase promoter. Labeling reactions consist of combining 2 μL DNA template (1 μg DNA), 1 μL each of 10 mM ATP, CTP and GTP, 0.75 μL 10 mM UTP, 2.5 μL 1 mM 6,8-difluoro-7-hydroxy-4-methylcoumarin-3-acetic acid conjugate of UTP (Prepared as in Example 36, only using 5-(3-aminoallyl)-uridine-5'-triphosphate, ammonium salt (Sigma Chemical) in place of 5-(3-aminoallyl)-2'-deoxyuridine-5'-triphosphate, ammonium salt), 2 μL 10× transcription buffer (400 mM Tris, pH 8.0, 100 mM MgCl$_2$, 20 mM spermidine, 100 mM NaCl), 1 μL T3 RNA polymerase (40 units/μL), 1 μL 2 mg/mL bovine serum albumin, and 8.75 μL water. Reactions are incubated at 37° C. for two hours.

The DNA template is removed by treatment of the reaction with 20 units DNase I for 15 minutes, at 37° C. The RNA transcript is then purified by extraction with an equal volume of phenol:chloroform, 1:1, then by chromatography through a G50 gel filtration column. Labeled RNA is denatured by heating for 5 minutes at 50° C., then hybridized to cellular preparations using standard procedures. When preparations are washed and viewed through a coumarin filter set on a fluorescence microscope, cells expressing actin mRNA show bright blue fluorescence.

Example 46

The use of 6,8-difluoro-7-hydroxy-4-methylcoumarinyl phosphate (6) for the detection of acid phosphatase activity:

The utility of Compound 6 as a substrate for both alkaline and acid phosphatase is compared with the utility of the non-fluorinated analog, 4-methylumbelliferyl phosphate (MUP).

Figure 4:
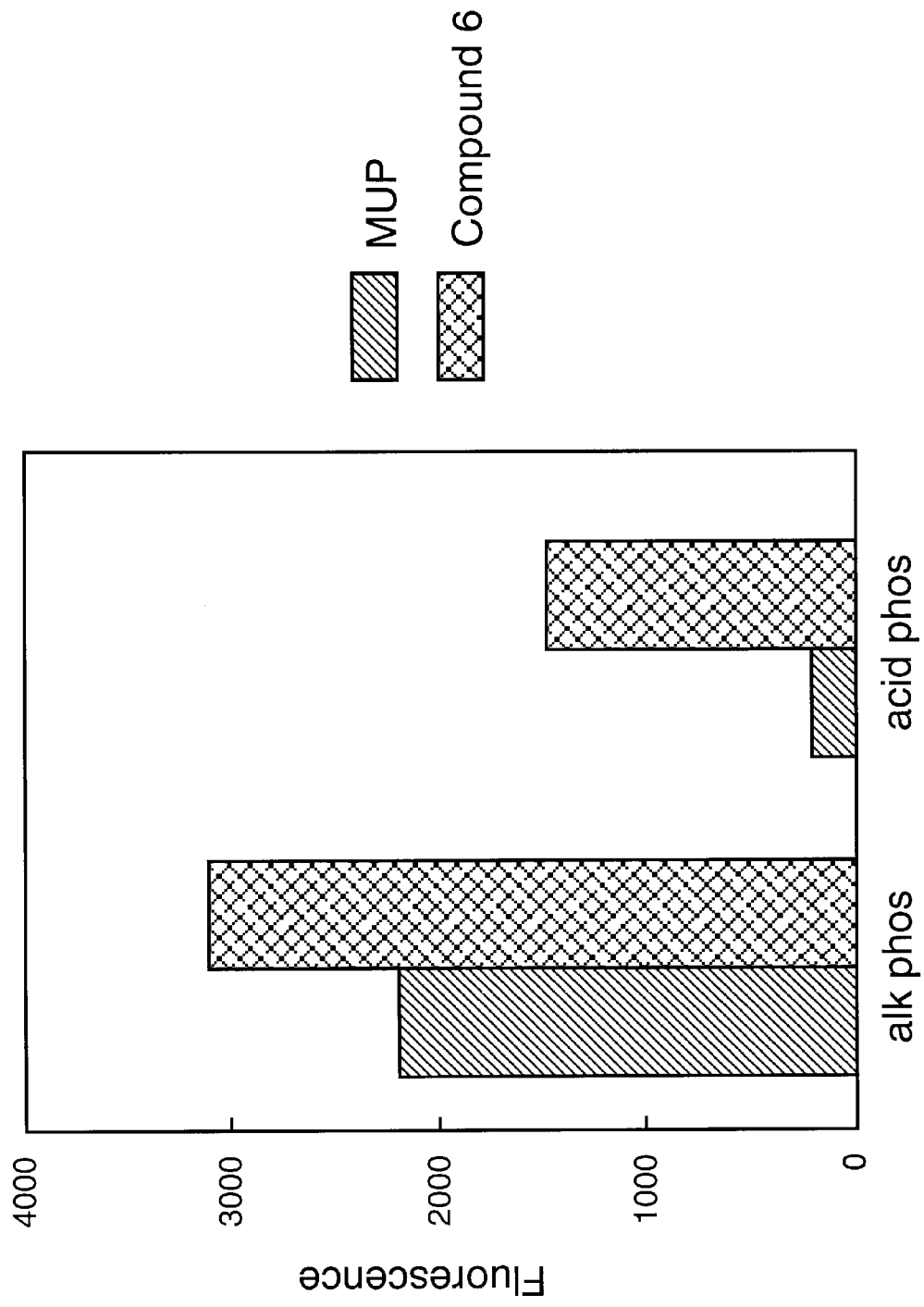
FIG. 4: A comparison of the relative reactivity of alkaline and acid phosphatase with respect to phosphatase substrates 6,8-difluoro-7-hydroxy-4-methylcoumarin phosphate (Compound 6) and 4-methylumbelliferyl phosphate (MUP). As indicated in Example 46, the use of Compound 6 produces higher fluorescence than the use of MUP.
Figure 5:
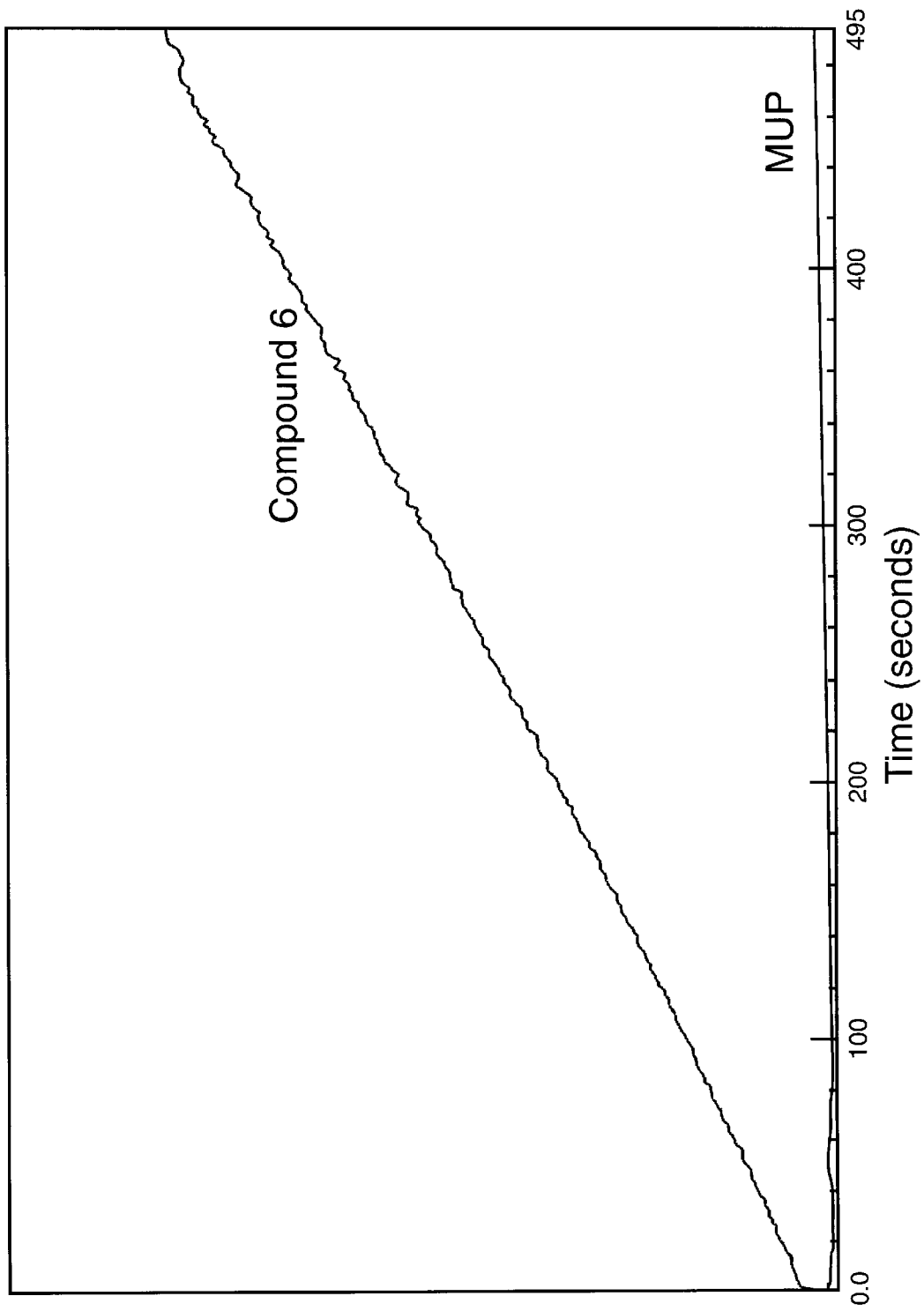
FIG. 5: A comparison of initial reaction rate of acid phosphatase with respect to phosphatase substrates Compound 6 and MUP, as described in Example 46.

1) Fluorescence yield: For an accurate comparison, the concentrations of the two substrates (initially approximately 10 mM) are matched by normalizing the absorbance of each substrate solution at 319 nm (pH 10) to a value of 0.52 (assuming the extinction coefficient of each substrate is approximately equivalent). The matched samples are then diluted 1:10 into excess enzyme buffer (10 units/mL), and the resulting fluorescence signal is recorded as a function of time (excitation 360 nm, emission 450 nm). The fluorescence yield obtained with acid phosphatase (pH 4.8, citrate buffer) is about 10 times greater when using Compound 6 than that obtained using MUP after one hour (FIG. 4). Even after raising both reaction solutions to pH 10 (thereby maximizing the fluorescence of the methylumbelliferone product), the signal from the reaction with Compound 6 is still twice as large as that obtained using MUP. Using alkaline phosphatase (pH 10.4, glycine buffer with 1 mM MgCl$_2$) the fluorescence yield obtained using Compound 6 is approximately 25% greater than that obtained using MUP (FIG. 4);

2) Reaction rate: Using a large excess of each substrate (50 mM to 0.01 units enzyme/mL), at pH 4.8 (citrate buffer) the initial reaction rate of hydrolysis of Compound 6 in the presence of acid phosphatase is significantly higher than that observed using MUP (FIG. 5). As above, the substrate samples are matched in concentration by normalizing absorbance values at 316 nm to a value of 0.525, then diluting 1:10.

Figure 6:
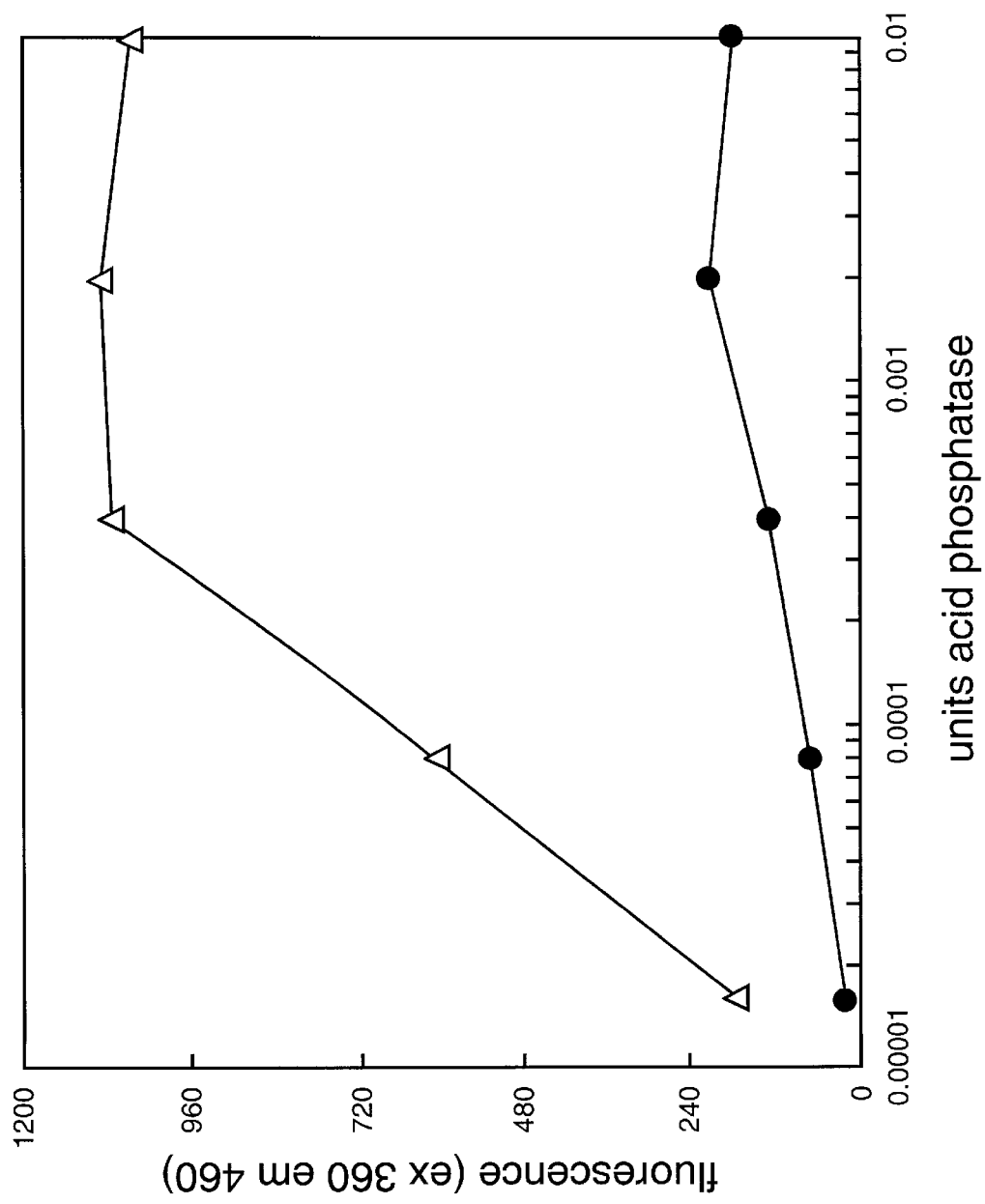
FIG. 6: A comparison of sensitivity of acid phosphatase detection possible using phosphatase substrates Compound 6 (Δ) and MUP (●). As described in Example 46, the use of Compound 6 allows the detection of significantly smaller amounts of phosphatase enzyme.
Figure 7:
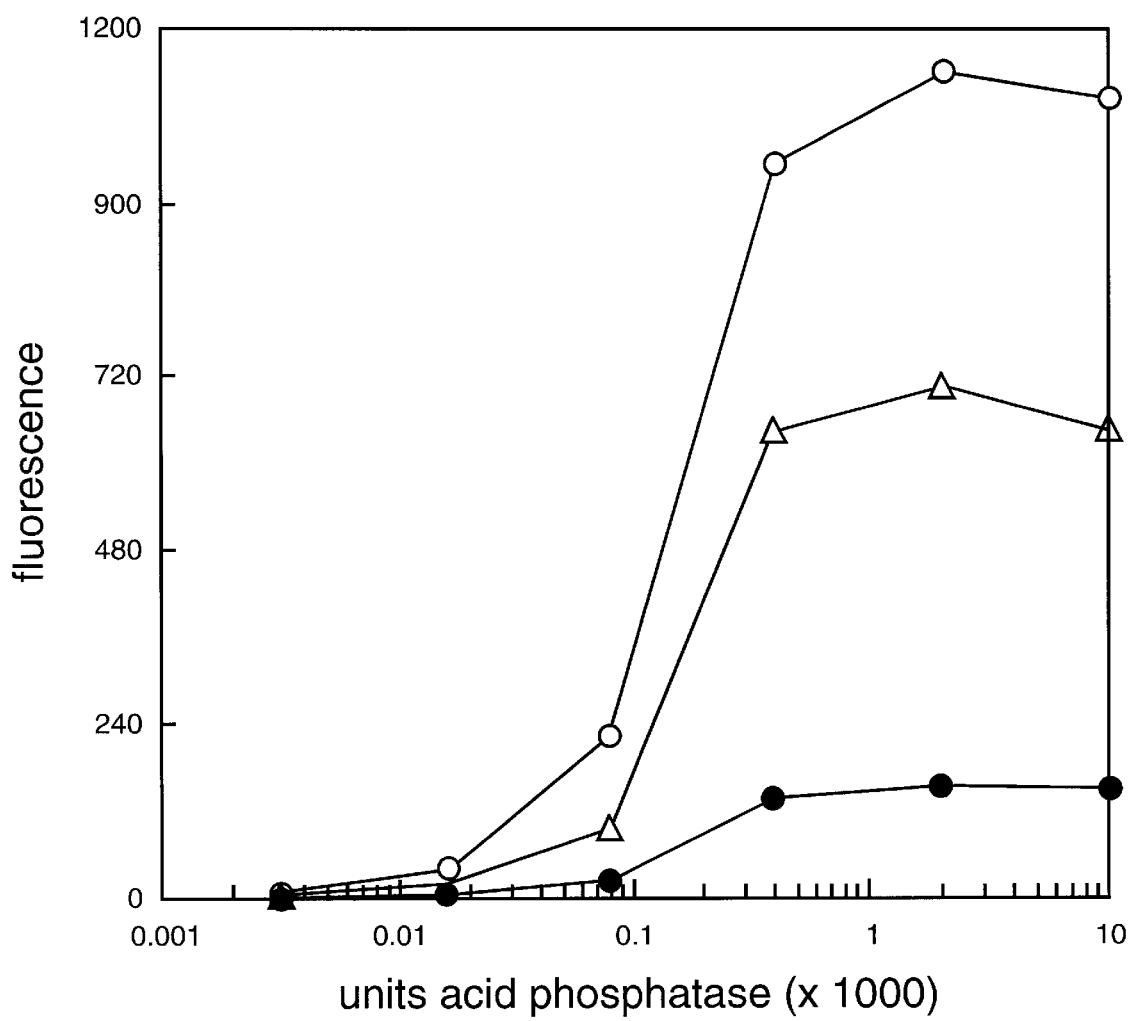
FIG. 7: A comparison of sensitivity of acid phosphatase detection possible using phosphatase substrates Compound 6 at pH 5 (○), MUP at pH 5 (●), and MUP at a final pH of 10 (Δ). As described in Example 46, the use of Compound 6 allows the detection of significantly lower amounts of phosphatase enzyme.

3) Enzyme sensitivity: Serial dilutions of acid phosphatase are incubated with 50 μM of each substrate for 1 hour at pH 5, then fluorescence intensity at 460 nm is collected following 360 nm excitation. FIGS. 7 and 6 show that over a wide range of enzyme concentrations (0.00001 to 10 units/mL), the use of Compound 6 provides a concentration detection threshold approximately 10-fold lower than is possible using MUP. Even after the reaction mixture is raised to a pH of 10, the substrate Compound 6 is still approximately twice as sensitive to enzyme concentration than MUP.

Example 47

The use of 6,8-difluoro-7-hydroxy-4-methylcoumarinyl galactoside (Compound 9) for the detection of β-galactosidase activity:

The utility of Compound 9 as a substrate for β-galactosidase is compared with the utility of the non-fluorinated analog, 4-methylumbelliferyl β-D-galactoside (MUG).

Figure 8:
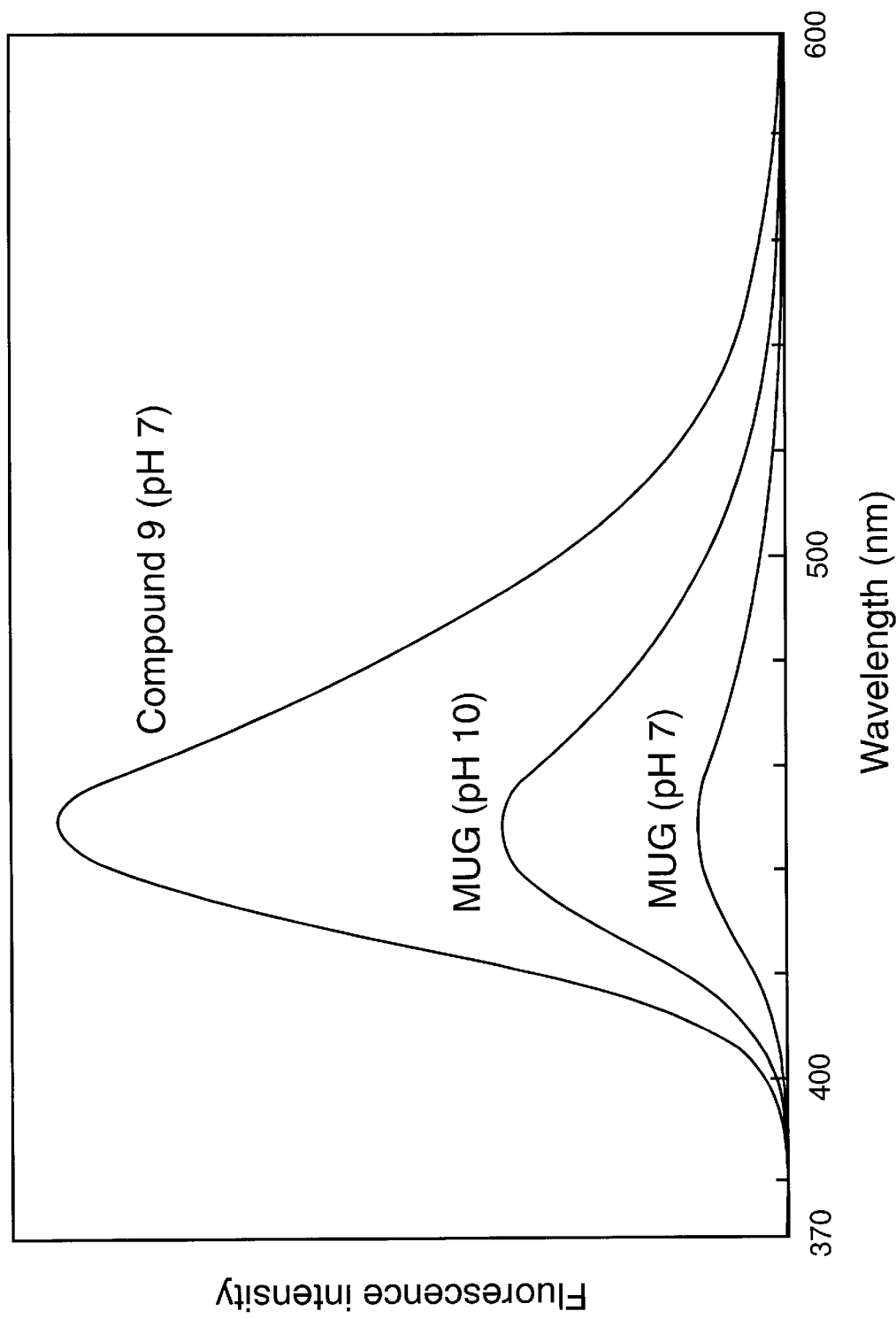
FIG. 8: The fluorescence spectra obtained from equal concentrations of 6,8-difluoro-7-hydroxy-4- methylcoumarin galactoside (Compound 9) and 4-methylumbelliferyl galactoside (MUG) when treated with equal amounts of β-galactosidase enzyme, at pH 7. As described in Example 47, even when the fluorescence of the product from MUG is enhanced (pH=10), the fluorescence of the assay solution using MUG is significantly less than that obtained using Compound 9.

1) Fluorescence yield: For an accurate comparison, the concentrations of the two substrates (initially approximately 10 mM) are matched by normalizing the absorbance of each substrate solution at 316 nm (pH 8.3; 20 mM sodium bicarbonate) to a value of 0.5 (assuming the extinction coefficient of each substrate is approximately equivalent). The matched samples are then diluted 1:10 into β-galactosidase buffer pH 7.0, and 2 units enzyme/mL are added. The emission spectra of the free dyes are recorded (460 nm, excited at 360 nm), and are given in FIG. 8. The use of Compound 9 as an enzyme substrate produces an approximately 8-fold signal enhancement over the use of MUG, when the fluorescence is measured at the reaction pH. Because the pKa of the coumarin obtained from deglycosylation of MUG is 7.8, the addition of NaOH to the MUG reaction solution to raise the pH to 10 optimizes the resulting fluorescence signal. However, even after optimization, the signal derived using Compound 9 (at pH 7.0) is still approximately 4-fold greater than that obtained using MUG (at pH 10).

2) $K_m$ determination: In a series of experiments, increasing amounts of each substrate are incubated with 0.01 units of β-galactosidase for 1 hour. The resulting fluorescence is measured by exciting at 360 nm, and the emission is collected at 460 nm. FIG. 9 shows that the $K_m$ value determined for Compound 9 is about 25 μM, whereas that derived for MUG is about 60 μM.

3) Reaction rate: The fluorescence yield is measured at high substrate concentrations (50 μM) (relative to low enzyme concentration (0.01 units/mL)) over the course of 1 hour to compare reaction rates. FIG. 10 shows Compound 9 to react more rapidly with β-galactosidase than does MUG.

4) Enzyme sensitivity: Serial dilutions of μ-galactosidase are incubated with 50 μM of each substrate for 1 hour at pH 7, then fluorescence intensity at 460 nm is collected (following 360 nm excitation). FIG. 11 shows that at the use of Compound 9 at the pH of the enzyme reaction provides a concentration detection threshold approximately 10-fold lower than is possible using MUG.

Example 48

Figure 1:
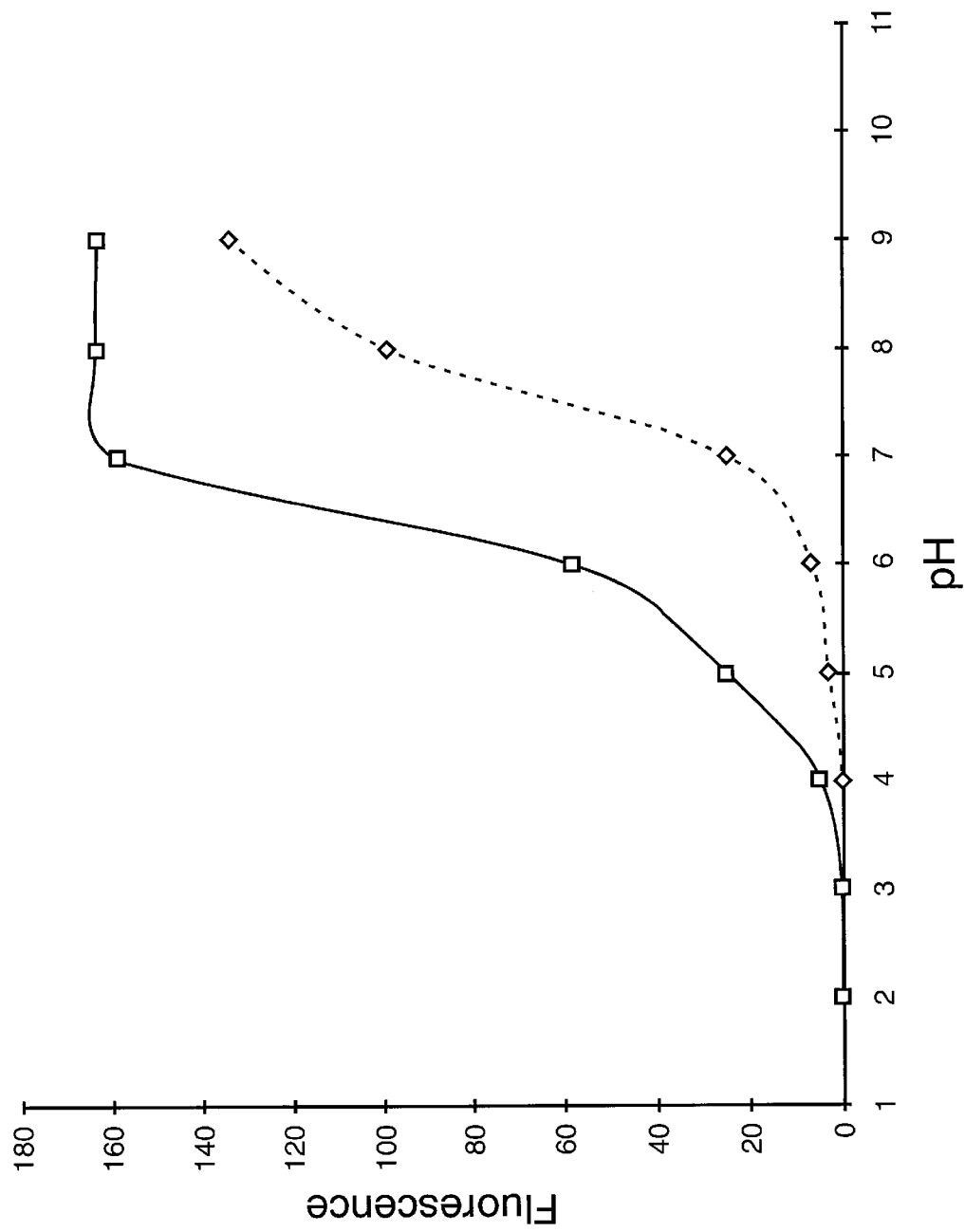
FIG. 1: A comparison of the pH-dependent fluorescence of 6,8-difluoro-7-hydroxy-4-methylcoumarin (Compound 4, □) and 7-hydroxy-4-methylcoumarin (◊), as described in Example 48.

Procedure for pH titration of fluorinated fluorophores:

The dye of interest is first dissolved in a series of buffers that have each been calibrated using a pH meter. Acetate buffers are typically used in the range of pH 4–6, and phosphate buffers in the pH range 6–8. Absorption measurements are made using solutions that are approximately 10 μM in concentration, and fluorescence measurements are made using solutions that are approximately 1 μM in concentration. The absorption or emission data is then plotted versus pH to determine pKa values. For example FIG. 1 shows the fluorescence emission data for 6,8-difluoro-7-hydroxy-4-methylcoumarin3-acetic acid (Compound 11, $pK_a$ ~6.2) and 7-hydroxy-4-methylcoumarin-3-acetic acid ($pK_a$ ~7.4) plotted versus the pH of the solution. The data shows that fluorination of the fluorophore has significantly lowered the $pK_a$ of the 7-hydroxycoumarin.

It is to be understood that, while the foregoing invention has been described in detail by way of illustration and example, numerous modifications, substitutions, and alterations are possible without departing from the spirit and scope of the invention as described in the following claims.

What is claimed is:

1. A compound having the formula

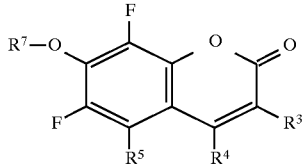

wherein $R^3$ is H, $C_1$–$C_8$ alkyl, $C_1$–$C_{18}$ perfluoroalkyl, CN, formyl, aryl, heteroaryl, arylcarbonyl, or —(C=O)—$NR^1R^2$ where $R^1$ and $R^2$ are independently H, $C_1$–$C_6$ alkyl, aryl, or $R^1$ and $R^2$ taken in combination are —$(CH_2)_2$—M—$(CH_2)_2$— where M is a single bond, —O—, —$CH_2$—, or —$NR^6$—, where $R^6$ is H or $C_1$–$C_6$ alkyl; or $R^3$ is —L—$R_X$ or —L—$S_C$;

$R^4$ is H, OH, CN, $C_1$–$C_{18}$ is alkyl, $C_1$–$C_{18}$ perfluoroalkyl, sulfomethyl, biologically compatible salt of sulfomethyl, halomethyl, aryl, —L—$R_X$ or —L—$S_C$;

$R^5$ is H or $C_1$–$C_6$ alkoxy;

$R^7$ is H, or a monovalent moiety derived by removal of a hydroxy group from a phosphate, a thiophosphate, a sulfate, or a biologically compatible salt thereof; or a monovalent moiety derived by removal of a hydroxy group from a carboxy group of an aliphatic or aromatic carboxylic acid; or a monovalent moiety derived by removal of a hydroxy group from an alcohol or from a mono- or polysaccharide; or $R^7$ is a photolabile caging group;

wherein aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;

heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$–$C_6$ alkyl, or $C_1$–$C_6$ alkoxy;

each L is independently a single covalent bond, or L is a covalent linkage having 1–24 nonhydrogen atoms selected from the group consisting of C, N, O and S and is composed of any combination of single, double, triple or aromatic carbon—carbon bonds, carbon-nitrogen bonds, nitrogen—nitrogen bonds, carbon-oxygen bonds and carbon-sulfur bonds;

$R_X$ is a reactive group;

$S_C$ is a conjugated substance;

provided that at least one of $R^3$ and $R^4$ is —L—$R_X$ or —L—$S_C$; or that $R^7$ is not hydrogen; or both.

2. A compound, as claimed in claim 1, wherein at least one of $R^3$ and $R^4$ is —L—$R_X$.

3. A compound, as claimed in claim 2, wherein $R_X$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carboxylic acid, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, or a thiol group.

4. A compound, as claimed in claim 3, wherein $R_X$ is a carboxylic acid, an activated ester of a carboxylic acid, an amine, a maleimide, an iodoacetamide, an isothiocyanate, a dichloro-s-triazine, or a halomethyl.

5. A compound, as claimed in claim 2, wherein $R^3$ is —L—$R_X$ and $R_X$ is a succinimidyl ester.

6. A compound, as claimed in claim 1, wherein $R^4$ is sulfomethyl, salt of sulfomethyl, halomethyl, $C_1$–$C_{18}$ alkyl or $C_1$–$C_{18}$ perfluoroalkyl.

7. A compound, as claimed in claim 1, wherein at least one of $R^3$ and $R^4$ is —L—Sc and $R^7$ is H.

8. A compound, as claimed in claim 7, wherein $S_C$ is an amino acid, a peptide, a protein, a monosaccharide, a polysaccharide, an ion-complexing moiety, a nucleotide, an oligonucleotide, a nucleic acid, a hapten, a drug, a toxin, a lipid, a phospholipid, a lipoprotein, a lipopolysaccharide, a liposome, a lipophilic polymer, a non-biological organic polymer, a polymeric microparticle, an animal cell, a plant cell, a bacterium, a yeast, or a virus.

9. A compound, as claimed in claim 8, wherein $S_C$ is an amino acid, a peptide, a protein, a nucleotide, an oligonucleotide, a nucleic acid, a monosaccharide, a polysaccharide, a drug, a toxin, or a tyramide.

10. A compound, as claimed in claim 9, wherein $S_C$ is a peptide or a protein.

11. A compound, as claimed in claim 9, wherein $S_C$ is a nucleoside, nucleotide or oligonucleotide.

12. A compound, as claimed in claim 7, wherein $S_C$ is further substituted by one or more dyes that are the same or different.

13. A compound, as claimed in claim 1, wherein $R^3$ is aryl or heteroaryl.

14. A compound, as claimed in claim 1, wherein
$R^3$ is H;
$R^4$ is methyl, sulfomethyl, salt of sulfomethyl, chloromethyl, or a $C_{11}$–$C_{18}$ alkyl; and
$R^5$ is H.

15. A compound, as claimed in claim 14, wherein $R^7$ is a monovalent moiety derived by removal of a hydroxy group from a phosphate or a salt of phosphate.

16. A compound, as claimed in claim 14, wherein $R^7$ is a monovalent moiety derived by the removal of a hydroxy group from an aliphatic carboxylic acid having 1–18 carbons, guanidinobenzoic acid, or sulfuric acid; or a biologically compatible salt thereof.

17. A compound, as claimed in claim 14, wherein $R^7$ is a monovalent moiety derived by removal of a hydroxy group from an alcohol having 1–6 carbons; or a monovalent moiety derived by removal of a hydroxy group from a mono- or polysaccharide.

18. A compound, as claimed in claim 17, wherein the monosaccharide is β-D-galactose, β-D-glucose, β-D-glucuronic acid, N-acetylglucosamine, or N-acetylgalactosamine.

19. A compound, as claimed in claim 1, wherein
$R^3$ has the formula

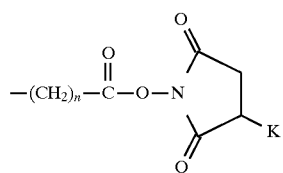

wherein
n=0–5; and
K is H, sulfonic acid, or a salt of sulfonic acid;
$R^4$ is H or methyl; and
$R^5$ is H.

20. A method of detecting the activity of an enzyme, comprising:
a) combining a sample suspected of containing the enzyme, with a substrate of the formula:

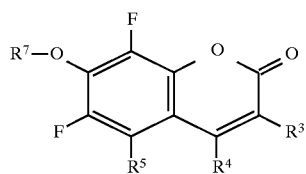

wherein
$R^3$ is H, $C_1$–$C_{18}$ alkyl, $C_1$–$C_{18}$ perfluoroalkyl, CN, formyl, aryl, heteroaryl, arylcarbonyl, or —(C=O)—$NR^1R^2$ where $R^1$ and $R^2$ are independently H, $C_1$–$C_6$ alkyl, aryl, or $R^1$ and $R^2$ taken in combination are —(CH$_2$)$_2$—M—(CH$_2$)$_2$— where M is a single bond, —O—, —CH$_2$—, or —NR$^6$—, where $R^6$ is H or $C_1$–$C_6$ alkyl; or $R^3$ is —L—$S_C$;
$R^4$ is H, OH, CN, $C_1$–$C_{18}$ alkyl, $C_1$–$C_{18}$ perfluoroalkyl, sulfomethyl, salt of sulfomethyl, halomethyl, aryl, or —L—$S_C$;
$R^5$ is H or $C_1$–$C_6$ alkoxy;
$R^7$ is a monovalent moiety derived by removal of a hydroxy group from a phosphate, a thiophosphate, a sulfate, or a biologically compatible salt thereof; or a monovalent moiety derived by removal of a hydroxy group from a carboxy group of an aliphatic or aromatic carboxylic acid; or a monovalent moiety derived by removal of a hydroxy group from an alcohol or from a mono- or polysaccharide;

wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamino;
heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$–$C_6$ alkyl, or $C_1$–$C_6$ alkoxy;
each L is independently a single covalent bond, or L is a covalent linkage having 1–24 nonhydrogen atoms selected from the group consisting of C, N, O and S and is composed of any combination of single, double, triple or aromatic carbon—carbon bonds, carbon-nitrogen bonds, nitrogen—nitrogen bonds, carbon-oxygen bonds and carbon-sulfur bonds;
$S_C$ is a conjugated substance
under conditions suitable for cleavage of the $R^7$-oxygen bond; and
b) detecting the resulting fluorescence either qualitatively or quantitatively.

21. A method, as claimed in claim 20, wherein the enzyme is a glycosidase.

22. A method, as claimed in claim 21, wherein $R^7$ is a monovalent moiety derived by removal of a hydroxy group from a monosaccharide that is β-D-galactose, β-D-glucose β-D-glucuronic acid, N-acetylglucosamine, or N-acetylgalactosamine.

23. A method, as claimed in claim 20, wherein the enzyme is a phosphatase.

24. A method, as claimed in claim 20, wherein said enzyme is present as a result of expression of a transfected gene, or as a result of cell secretion.

25. A method, as claimed in claim 20, wherein
$R^3$ is H, aryl, heteroaryl, or —L—$S_C$;
$R^4$ is $CH_3$, $CF_3$, sulfomethyl, salt of sulfomethyl, halomethyl, $C_{11}$–$C_{18}$ alkyl, or —L—$S_C$;
$R^5$ is H.

26. A method, as claimed in claim 25 wherein $R^4$ is halomethyl.

27. A method, as claimed in claim 25 wherein $S_C$ is a tyramine and the enzyme is a peroxidase.

28. A method of detecting a complementary member of a specific binding pair in a sample, comprising:

a) adding to said sample a dye-conjugate of a first member of a specific binding pair for which there is a complementary member, to which is attached one or more dye molecules, which may be the same or different, having the formula

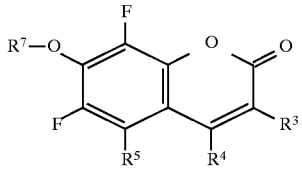

wherein
$R^3$ is H, $C_1$–$C_{18}$ alkyl, $C_1$–$C_{18}$ perfluoroalkyl, CN, formyl, aryl, heteroaryl, arylcarbonyl; or $R^3$ is —L—$S_C$;

$R^4$ is H, OH, CN, $C_1$–$C_{18}$ alkyl, $C_1$–$C_{18}$ perfluoroalkyl, sulfomethyl, salt of sulfomethyl, aryl, or —L—$S_C$;

$R^5$ is H or $C_1$–$C_6$ alkoxy;

$R^7$ is H, or a monovalent moiety derived by removal of a hydroxy group from a phosphate, a thiophosphate, a sulfate, or a biologically compatible salt thereof; or a monovalent moiety derived by removal of a hydroxy group from a carboxy group of an aliphatic or aromatic carboxylic acid or of an amino acid, protected amino acid, peptide, or protected peptide; or a monovalent moiety derived by removal of a hydroxy group from an alcohol or from a mono- or polysaccharide; or $R^7$ is a photolabile caging group;

wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;

heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$–$C_6$ alkyl, or $C_1$–$C_6$ alkoxy;

each L is independently a single covalent bond, or L is a covalent linkage having 1–24 nonhydrogen atoms selected from the group consisting of C, N, O and S and is composed of any combination of single, double, triple or aromatic carbon—carbon bonds, carbon-nitrogen bonds, nitrogen—nitrogen bonds, carbon-oxygen bonds and carbon-sulfur bonds;

provided that at least one of $R^3$ and $R^4$ is —L—$S_C$; where $S_C$ is a conjugated substance that is the first member of the specific binding pair;

b) allowing sufficient time for the dye-conjugate to form a complex with the complementary member, said complex exhibiting a detectable optical response; and c) detecting the complex to locate the complementary member.

29. A method, as claimed in claim 28, wherein the optical response is a fluorescence response.

30. A method, as claimed in claim 28, wherein the first member of the specific binding pair is a peptide, a protein, a nucleotide, an oligonucleotide, a nucleic acid polymer, a drug, a toxin, or a polysaccharide.

31. A method, as claimed in claim 28, wherein the first member of the specific binding pair comprises an antibody, an antibody fragment, an avidin, a streptavidin, a lectin or an enzyme.

32. A method, as claimed in claim 28, wherein the complementary member is present in a cell, bacteria, virus or yeast cell, or is immobilized on a polymer, polymeric membrane or polymeric particle.

33. A method, as claimed in claim 29, further comprising distinguishing the fluorescence response from that of a second fluorophore having detectably different optical properties.

34. A method, as claimed in claim 29, wherein the fluorescence response is detected using a flow cytometer, further comprising sorting said complex based on the fluorescence response.

35. A compound having the formula

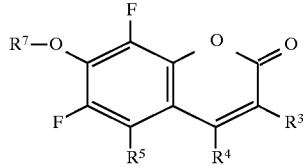

wherein
$R^3$ is H, $C_1$–$C_{18}$ alkyl, $C_1$–$C_{18}$ perfluoroalkyl, CN, formyl, aryl, heteroaryl, arylcarbonyl, or —(C=O)—$NR^1R^2$ where $R^1$ and $R^2$ are independently H, $C_1$–$C_6$ alkyl, aryl, or $R^1$ and $R^2$ taken in combination are —(CH$_2$)$_2$—M—(CH$_2$)$_2$— where M is a single bond, —O—, —CH$_2$—, or —NR$^6$—, where $R^6$ is H or $C_1$–$C_6$ alkyl;

$R^4$ is H, OH, CN, $C_1$–$C_{18}$ alkyl, $C_1$–$C_{18}$ perfluoroalkyl, sulfomethyl, biologically compatible salt of sulfomethyl, halomethyl, or aryl;

$R^5$ is; H or $C_1$–$C_6$ alkoxy;

$R^7$ is H;

wherein
aryl is an aromatic substituent having 6 conjugated carbon atoms that is optionally and independently substituted by H, halogen, cyano, sulfo, biologically compatible salts of sulfo, carboxy, nitro, alkyl, perfluoroalkyl, alkoxy, alkylthio, amino, monoalkylamino, dialkylamino or alkylamido;

heteroaryl is a 5- or 6-membered aromatic heterocycle that is optionally fused to additional six-membered aromatic rings, or is fused to one 5- or 6-membered heteroaromatic ring, said heteroaromatic rings containing at least 1 and as many as 3 heteroatoms that are selected from the group consisting of O, N and S in any combination, that is attached by a single bond, and is optionally and independently substituted by H, halogen, $C_1$–$C_6$ alkyl, or $C_1$–$C_6$ alkoxy.

* * * * *